(12) United States Patent
Vitek et al.

(10) Patent No.: US 6,410,598 B1
(45) Date of Patent: Jun. 25, 2002

(54) COMPOSITIONS AND METHODS FOR ADVANCED GLYCOSYLATION ENDPRODUCT-MEDIATED MODULATION OF AMYLOIDOSIS

(76) Inventors: Michael P. Vitek, 205 Park Knoll La., Apex, NC (US) 27502; Anthony Cerami, Ram Island Dr., Shelter Island, NY (US) 11964; Richard J. Bucala, 504 E. 63rd St. Apt. 33-0, New York, NY (US) 10021; Peter C. Ulrich, 148 DeWolf Rd., Old Tappan, NJ (US) 07675; Helen Vlassara, Ram Island Dr., Shelter Island, NY (US) 11964; Xini Zhang, 150 Fairhaven Dr. Apt. D1, Jericho, NY (US) 11753

( * ) Notice: Subject to any disclaimer, the term of this patent is extended or adjusted under 35 U.S.C. 154(b) by 0 days.

(21) Appl. No.: 08/477,364

(22) Filed: Jun. 7, 1995

(Under 37 CFR 1.47)

Related U.S. Application Data

(63) Continuation-in-part of application No. 08/457,169, filed on Jun. 1, 1995, which is a continuation-in-part of application No. PCT/US95/01380, filed on Feb. 2, 1995, which is a continuation-in-part of application No. 08/311,768, filed on Sep. 23, 1994, now abandoned, which is a continuation of application No. 08/191,579, filed on Feb. 3, 1994, now abandoned.

(51) Int. Cl.[7] ........................ A01N 37/52; A61K 31/155

(52) U.S. Cl. ..................... 514/632; 514/634; 514/20; 514/229.8; 514/331

(58) Field of Search .................... 514/632, 634, 514/400, 562, 866, 20, 45, 229.8, 331

(56) References Cited

U.S. PATENT DOCUMENTS

| | | | |
|---|---|---|---|
| 4,665,192 A | | 5/1987 | Cerami et al. |
| 4,758,583 A | | 7/1988 | Cerami et al. |
| 4,761,368 A | | 8/1988 | Cerami et al. |
| 4,900,747 A | | 2/1990 | Vlassara et al. |
| 4,908,446 A | | 3/1990 | Ulrcih et al. |
| 4,983,604 A | | 1/1991 | Ulrich et al. |
| 5,017,696 A | | 5/1991 | Farmar et al. |
| 5,126,442 A | | 6/1992 | Farmar et al. |
| 5,128,360 A | * | 7/1992 | Cerami et al. ............... 514/400 |
| 5,130,324 A | | 7/1992 | Ulrich et al. |
| 5,140,048 A | | 8/1992 | Farmar et al. |
| 5,242,932 A | | 9/1993 | Gandy et al. |
| 5,276,059 A | | 1/1994 | Caughey et al. |
| 5,326,779 A | | 7/1994 | Ulrich et al. |
| 5,334,617 A | * | 8/1994 | Ulrich et al. ............... 514/562 |
| 5,367,052 A | | 11/1994 | Cooper et al. |

FOREIGN PATENT DOCUMENTS

| | | | | |
|---|---|---|---|---|
| EP | | 0222313 | 5/1987 | |
| EP | | 0259893 | 3/1988 | |
| EP | | 0316852 | 5/1989 | |
| WO | | WO 92/14697 | 9/1992 | |
| WO | | 92/19236 | 11/1992 | |
| WO | | WO 93/03714 | 3/1993 | |
| WO | | WO93/04690 | 3/1993 | |
| WO | | WO 93/13421 | 7/1993 | |
| WO | | WO 93/14750 | 8/1993 | |
| WO | | 9314750 | * 8/1993 | ......... A61K/31/195 |
| WO | | WO 93/23081 | 11/1993 | |

OTHER PUBLICATIONS

Cooper et al (1987) Proc. Nat'l. Acad. Sci. 84:8628–8632.*
Clark et al (1987) The Lancet 2(8553):231–234.*
Brownlee et al (1986) Science 232:1629–1632.*
Hammes et al (1994) Diabetalogia 37:3235.*
Roitt, 1991, In Essent. Immun., Blackwell Sci. Pub., pp65–8 & 74.
Edgington, 1994, Bio/Technology 12:591–94.
Lorenzo et al., 1994, Nature 368:756–760.
Smith et al.,1994, Proc. Natl. Acad. Sci. USA 91:5710–4.
Vitek et al., 1994, Proc. Natl. Acad. Sci. USA 91:4766–70.
Vlassara et al., 1994, J. Lab. clin. Med. 124:19–30.
Yan et al., 1994, Proc. Natl. Acad. Sci. USA 91:7787–91.
Yan et al., 1994, J. Biol. Chem. 269:9889–97.
Amiel, 1993, Lancet 341:1249–50.
Cai et al. 1993, Science 259:514–6.
Gregoriadis et al., 1993, Trends in Biotech. 11:440–2.
Jarrett et al. , 1993,Biochemistry 32:4693–7.
Jarrett et al., 1993, Cell 73:1055–1058.
Miyata et al., 1993, Cell 73:1055–8.
Oosawa et al.,1993, Soc. Neurosci. Abst. 19:1038 (Abstract #422.7).
Pike et al., 1993, J. Neurosci. 13:1676–87.
Roher et al., 1993, J. Biol. Chem. 268:3072–3083.

(List continued on next page.)

*Primary Examiner*—Patricia A. Duffy

(57) ABSTRACT

The present invention relates generally to the non-enzymatic glycosylation of amyloidogenic proteins and the consequent formation of advanced glycosylation endproducts (AGEs). It has been found that formation of AGE-amyloidogenic proteins can enhance amyloidosis. The invention further relates to compositions and methods for the prevention and treatment of amyloidosis associated with amyloid diseases, particularly neurodegenerative disease and Type II diabetes, and more particularly Alzheimer's disease. In a specific example, aggregation of an amyloidogenic peptide, βAP, is enhanced by the glycosylation reaction of βAP to form AGE-βAP as defined herein. Accordingly, the invention extends to a method for modulating the in vivo aggregation of amyloid polypeptides and associated amyloidosis by controlling the formation and presence of AGE-amyloid polypeptide. A corresponding diagnostic utility comprises the measurement of the course and extent of amyloidosis by a measurement of the presence and amount of AGEs and particularly, AGE-amyloid. An assay is included that may use the AGE-amyloid polypeptide of the present invention to identify disease states characterized by the presence of AGE-amyloid. Additionally, such an assay can be utilized to monitor therapy and thus adjust a dosage regimen for a given disease state characterized by the presence of AGE-amyloid.

5 Claims, 8 Drawing Sheets

OTHER PUBLICATIONS

Rozemuller et al., 1993, Am. J. Pathol. 142:1449–57.
Yan et al., 1993, Clin. Res. 41:190A.
Bucala et al., 1992, in Post–Translational Modifications of Proteins, Harding et al., Eds., CRC Press, Boca Raton 2:53–79.
Burdick et al., 1992, J. Biol. Chem. 267:546–554.
Fraser et al., 1992, Biochem. 31:10716–23.
Haan et al., 1992, Clin. Neuro. Neurosurg. 94:317–8.
Makita et al., 1992. J. Biol. Chem. 267:5133–38.
Shoji et al., 1992, Science 258:126–129.
Jacobsen et al., 1991, Neurobiol. Aging 12:585–592.
Kihara et al., 1991, Proc. Natl. Acad. Sci. USA 88:6107–11.
Pike et al., 1991, Eur. J. Pharm. 207:367–368.
Wisniewski et al., 1991, Biochem. Biophys. Res. Commun. 179:1247–54.
Wisniewski et al., 1991, Biochem. Biophys. Res. Commun. 180:1528.
Coe et al., 1990, J. Exp. Med. 171:1257–67.
Haan et al., 1990, Clin. Neurol. Neurosurg. 92:305–310.
Levy et al., 1990, Science 248:1124–26.
Frangione, 1989, Ann. Med. 21:69–72.
Glenner et al., 1989, N. Neurol. Sci. 94:1–28.
Hayase et al., 1989, J. Biol. Chem. 263:3758–3764.
Cooper et al., 1988, Proc. Natl. Acad. Sci. USA 85:7763–66.
Coria et al., 1988, Lab. Invest. 58:454–8.
Goldgaber et al., 1987, Science 235:8778–8780.
Kang et al., 1987, Nature 325:733–736.
Kascsak et al., 1987, J. Virol. 61:3688–3693.
Brownlee et al, 1986, Science 232:1629–1632.
Fingl et al., 1975, The Pharmacological Basis of Therapeutics, L.S. Goodman et al., eds., Macmillan Pub. Co., New York, pp. 1–46.

* cited by examiner

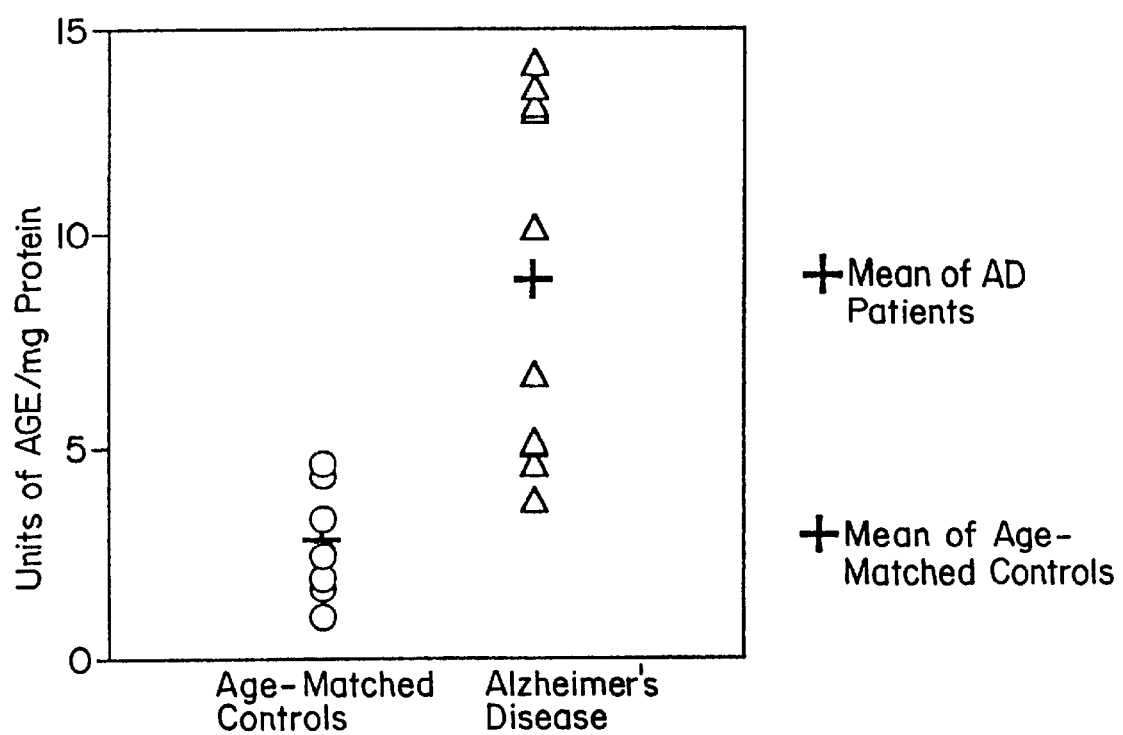

COMPOSITIONS AND METHODS FOR ADVANCED GLYCOSYLATION ENDPRODUCT-MEDIATED MODULATION OF AMYLOIDOSIS

RELATED APPLICATIONS

The present application is a Continuation-in-part of Application PCT/US95/01380, filed Feb. 2, 1995, which is a Continuation-in-part of U.S. application Ser. No. 08/311,768, filed Sep. 23, 1994, now abandoned, which is a Continuation-in-part of co-pending U.S. application Ser. No. 08/457,169, filed Jun. 1, 1995, which is a continuation of U.S. application Ser. No. 08/191,579, filed Feb. 3, 1994, now abandoned, of which the instant Application claims the benefit of the filing date pursuant to 35 U.S.C. §§ 120 and 365, and which is specifically incorporated herein by reference in its entirety.

FIELD OF THE INVENTION

The present invention relates generally to the non-enzymatic glycosylation of amyloid proteins and the often consequent formation of advanced glycosylation endproducts (AGEs). Formation of AGE-amyloid can result in disease conditions or complications. The invention particularly relates to compositions and methods for the prevention and treatment of amyloidosis associated with neurodegenerative diseases, in particular Alzheimer's disease, and amyloidosis associated with Type II (adult onset) diabetes.

BACKGROUND OF THE INVENTION

Amyloidosis and the B-Amyloid Peptide

Amyloidosis generally refers to a physiological condition which involves deposition of insoluble polypeptides, termed amyloid polypeptides or amyloid proteins. There are a wide range of amyloid proteins found in various tissues throughout a subject, and a number of pathological conditions associated with various amyloidoses. For example, multiple myeloma can result in amyloidosis with the immunoglobulin proteins. Idiopathic familial Mediterranean fever also involves systemic amyloidosis. Perhaps the best known disease associated with amyloidosis is Alzheimer's disease.

Alzheimer's disease (AD) affects more than 30% of humans over 80 years of age, and as such, represents one of the most important health problems of developed countries (Evans et al., 1989, JAMA 262:2551–56; Katzman and Saitoh, 1991, FASEB J. 280:278–286). The etiology and pathogenesis of this progressive dementia is poorly understood, but symptomatic disease is associated with deposits of amyloid plaques, cerebrovascular amyloid and neurofibrillary tangles in the brain and cerebrovasculature. The number of plaques in AD patients' brains are typically 5- to 10 fold greater than in age-matched healthy controls. Increased levels of plaques may result from increased rate of synthesis of the components of the plaques, decreased rate of degradation, or some combination of the two.

The primary protein component of plaques is the 42 amino acid (4.2 kDa) beta-Amyloid Peptide (βAP), which derives from a family of larger Amyloid Peptide Precursor (APP) proteins (Glenner and Wong, 1984, Biochem. Biophys. Res. Commun. 120:885–890; Glenner and Wong, 1984, Biochem. Biophys. Res. Commun. 122:1131–35; Goldgaber et al., 1987, Science 235:8778–8780; Kang et al., 1987, Nature 325:733–736; Robakis et al., 1987, Proc. Natl. Acad. Sci. USA 84:4190–4194; Tanzi et al., 1987, Science 235:880–884). The process of amyloidosis is poorly understood, but requires at least βAP. Recent evidence shows that βAP may be found in extracellular spaces like cerebrospinal fluid (CSF) of the brain and conditioned media of many cell types. Since increased amount& of amyloid deposits are present in AD brains, one simple hypothesis is that increased βAP production leads to increased amyloidosis. Messenger RNAs encoding the APP precursors of βAP increase about 2-fold in AD brains, which has suggested to some a possible 2-fold increase in rates of translation, which may explain increased amyloid plaque formation (e.g., Jacobsen et al., 1991, Neurobiol. Aging 12:585–592, and references cited therein; Palmert et al., 1989, Prog. Clin. Biol. Res. 317:971–984; Tanaka et al., 1990, Rinsho Byori 38:489–493; Tanaka et al., 1989, Biochem. Biophys. Res. Commun. 165:1406–1414). An example of an increased efficiency of βAP production that correlates with increased plaque levels is found in a rare genetically linked familial form of Alzheimer's disease (Cai et al., 1992, Science 259:514–516; Citron et al., 1992, Nature 360:672–674; Mullan et al., 1992, Nature Genet. 1:345–347), known as a Swedish disease involving a double lysine-methionine (KM) to asparagine-leucine (NL) mutation in APP near the amino-terminus of βAP. This mutation increases the release of extracellular βAP in cultured cells. However, while this observation may partly explain amyloidosis in the Swedish disease (and Down's Syndrome), βAP peptide levels in CSF of AD and healthy patients are the same (Oosawa et al., 1993, Soc. Neurosci. Abst. 19:1038; Shoji et al., 1992, Science 258:126–129). Thus, although healthy subjects appear to possess similar quantities of βAP as AD patients, they nevertheless fail to accumulate the high number and amount of amyloid plaques seen in their AD counterparts.

Post-translational events may contribute to amyloidosis. Beyond increased rates of translation, physiological events such as greater efficiency of βAP production from its precursor, aggregation into fibrillar structures, and resistance to proteolysis may unbalance degradative processes, resulting in plaque formation.

Aggregation of the components of amyloid is a critical step in the development of amyloidosis. Once formed, fibrillar aggregates of βAP are extremely stable and not easily degraded. Amyloid plaques may be purified by their resistance to solubilization in boiling SDS and digestion with a variety of proteases. Additional treatment with 80% formic acid or 6M guanidine thiocyanate eventually solubilizes a portion of the plaque material. The solubilized protein is primarily the 42 amino acid βAP. Yet even after these harsh denaturation treatments, dimers, tetramers and large molecular weight aggregates containing immunoreactive βAP are found. This resistance to solubilization into soluble or monomeric components suggests extensive protein modifications.

Further experiments have shown that primary neuronal cultures treated with full length βAP 1–42 in soluble form remain viable. Thus, soluble βAP 1–42 shows no toxicity. In contrast, cultures treated with insoluble aggregates of βAP 1–42 show a toxic response (Pike et al., 1991, Eur. J. Pharm. 207:367–368; Pike et al., 1993, J. Neurosci. 13:1676–87). This experiment suggests that the toxicity of βAP is related to its state of aggregation. Thus, an understanding of the mechanism forming fibrils and/or insoluble aggregates from soluble βAP may be critical to preventing toxicity and resulting neurodegenerative disease.

In the absence of increased soluble βAP in most cases of AD, the question remains how amyloid accumulates to a greater degree at different rates. Synthetic βAPs corresponding to the first 28, 40, or 42 amino acids of βAP (i.e., βAP 1–28, βAP 1–40 and βAP 142, respectively) display concentration-dependent aggregation kinetics in in vitro incubations. Fibrillar aggregates form in vitro and these appear similar to brain β-amyloid fibrils at the morphological level using electron microscopy and at the light microscopy and spectroscopic levels using Congo Red and Thioflavin stains.

The more rapid kinetics of aggregation observed at $\mu$M concentrations of soluble βAP in vitro are only of limited relevance for insight into the mechanism of fibril formation in vivo. At lower βAP concentrations, for instance in the physiological range of about 5 nM, there is a considerable lag period before measurable aggregate is formed in vitro. This observation suggests that the rate limiting step in aggregation could be formation of a "nucleus" or "seed" upon which additional βAP can rapidly accumulate.

Amylin, Pancreatic Islet Cells, and Type II Diabetes

There are two broad types of diabetes: Type I (childhood onset diabetes), which is associated with destruction of the pancreatic beta cells and loss of insulin, and other hormones, produced by these cells, and is treated with insulin; and Type II (adult onset diabetes), which is associated with insulin resistance. Type II diabetics can be further divided into Type IIA, characterized by high blood pressure, obesity and insulin resistance, and Type IIB, which includes lean individuals, obese insulin sensitive individuals, and young individuals. Perhaps the most significant distinction between Type I and Type II diabetes is the absence of autoimmune disease in Type II diabetes; otherwise, this syndrome is characterized by a similarly diverse array of symptoms and causes.

One common characteristic of Type II diabetics is the presence of amyloid plaques in the pancreas. Such plaques are found in 90% of Type II diabetics upon autopsy. As with Alzheimer's disease, the presence of amyloid plaques in the affected organ cannot be conclusively demonstrated until autopsy (see, Edgington, 1994, Bio/Technology 12:591). Two groups independently identified the major component of pancreatic amyloid plaques as a 37 amino acid polypeptide termed islet amyloid polypeptide (IAPP) (Westermark et al., 1987, Proc. Natl. Acad. Sci. USA 84:3881–85; Westermark et al., 1987, Am. J. Physiol. 127:414–417), or amylin (Cooper et al., 1987, Proc. Natl. Acad. Sci. USA 84:8628–32; Cooper et al., 1988, Proc. Natl. Acad. Sci. USA 85:7763–66); the peptides identified by both groups appear to be interchangeable (Amiel, 1993, Lancet 341:1249–50). In its soluble form, amylin antagonizes insulin, and thus appears to have a role in the regulation of bloodstream glucose levels (see, Edgington, supra).

However, at high concentration, amylin, like βAP, aggregates in a β-pleated sheet structure, and forms fibrils that appear to be toxic (Lorenzo et al., 1994, Nature 368:756–760). In particular, this paper reports that human amylin fibrils are toxic to insulin-producing β-cells of the adult pancreas of rats and humans. Amylin fibrils appear to induce islet cell apoptosis, leading to cell dysfunction and death in Type II diabetes mellitus (Lorenzo et al., supra).

Advanced Glycosylation Endproducts (AGEs)

The reaction between glucose and proteins has been known for some time. Its earliest manifestation was in the appearance of brown pigments during the cooking of food. In 1912, Maillard observed that glucose or other reducing sugars react with amino acids to form adducts that undergo a series of dehydrations and rearrangements to form stable brown pigments (Maillard, 1912, C.R. Acad. Sci. 154:66–68).

In the years that followed the initial discovery by Maillard, food chemists studied the hypothesized reaction in detail and determined that stored and heat-treated foods undergo nonenzymatic browning as a result of the reaction between glucose and polypeptide chains, and that the proteins thereby become crosslinked and exhibit decreased bioavailability. At this point, it was determined that the pigments responsible for the development of the brown color as a result of protein glycosylation possessed characteristic spectra and fluorescent properties; however, the chemical structure of the pigments had not been specifically elucidated.

The reaction between reducing sugars and food proteins discussed above was found in recent years to have its parallel in vivo. Thus, the nonenzymatic reaction between glucose and the free amino groups on proteins to form a stable amino, 1-deoxy ketosyl adduct, known as the Amadori product, has been shown to occur with hemoglobin, wherein a rearrangement of the amino terminal of the B-chain of hemoglobin by reaction with glucose forms the adduct known as hemoglobin $A_{1c}$. The reaction has also been found to occur with a variety of other body proteins, such as lens crystallin, collagen and nerve proteins (see Bunn et al., 1975, Biochem. Biophys. Res. Commun. 67:103–109; Koenig et al., 1975, J. Biol. Chem. 252:2992–2997; Monnier and Cerami, in *Maillard Reaction in Food and Nutrition*, ed. Waller, G. A., American Chemical Society 1983, pp. 431–448; and Monnier and Cerami, 1982, Clinics in Endocrinology and Metabolism 11:431–452).

Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 to 90 years (see Monnier and Cerami, 1981, Science 211:491–493; Monnier and Cerami, 1983, Biochem. Biophys. Acta 760:97–103; and Monnier et al., 1984, "Accelerated Age-Related Browning of Human Collagen in Diabetes Mellitus", Proc. Natl. Acad. Sci. USA 81:583–587). Interestingly, the aging of collagen can be mimicked in vitro in a much shorter period of time by crosslinking induced by incubation in solution with relatively high concentrations of glucose. The capture of other proteins and the formation of adducts by collagen, also noted, is theorized to occur by a crosslinking reaction, and is believed to. account, for instance, for the observed accumulation of albumin and antibodies in kidney basement membrane (see Brownlee et al., 1983, J. Exp. Med. 158:1739–1744; and Kohn et al., 1984, Diabetes 33:57–59).

Glucose and other reducing sugars attach non-enzymatically to the amino groups of proteins in a concentration-dependent manner. Over time, these initial Amadori adducts can undergo further rearrangements, dehydrations and cross-linking with other proteins to accumulate as a complex family of structures referred to as Advanced Glycosylation Endproducts (AGEs). Substantial progress has been made toward the elucidation of the role and clinical significance of advanced glycosylation endproducts, so that it is now acknowledged that many of the conditions heretofore attributed to the aging process or to the pathological effects of diseases such as diabetes, are attributable at least in part to the formation of AGEs in vivo.

As noted above, advanced glycosylation end products tend to accumulate on molecules with long half-lives, especially under conditions of relatively high sugar concentration. Thus, AGE accumulation can be indicative of protein half-life, sugar concentration, or both. These factors have important consequences. Numerous studies have suggested that AGEs play an important role in the structural and functional alteration which occurs during aging and in chronic disease. Additionally, advanced glycosylation endproducts are noted to accumulate to a greater extent in diabetic and other diseased tissue than in normal tissue.

The "family" of AGEs includes species which can be isolated and characterized by chemical structure, some being quite stable, while others are unstable or reactive. The reaction between reducing sugars and the reactive groups of proteins may initiate the advanced glycosylation process. This process typically begins with a reversible reaction between the reducing sugar and the reactive group to form a Schiff base, which proceeds to form a covalently-bonded Amadori rearrangement product. Once formed, the Amadori product undergoes further rearrangement to produce the AGE-modified compound.

In U.S. Pat. No. 4,665,192, a fluorescent chromophore was isolated and identified that was found to be present in certain browned polypeptides, such as bovine serum albumin and poly-L-lysine, and was assigned the structure 2-(2-furoyl)-4(5)-2(furanyl)-1H-imidazole. More recently, other advanced glycosylation products have been identified, e.g., as described in Farmar et al., U.S. Pat. No. 5,140,048, issued Aug. 18, 1992; pyrraline (Hayase et al., 1989, "Aging of Proteins: Immunological Detection of a Glucose-derived Pyrrole Formed during Maillard Reaction in Vivo", J. Biol. Chem. 263:3758–3764); and pentosidine (Sell and Monnier, 1989, "Structure Elucidation of a Senescence Cross-link from Human Extracellular Matrix", J. Biol. Chem. 264:21597–602).

Based on their knowledge of the role of AGEs in disease, the present inventors have sought to identify factors that enhance aggregation of βAP, and more importantly to identify agents and methods to inhibit the action of such factors and thus prevent amyloidosis, e.g., in Alzheimer's disease and other amyloid diseases. More particularly, the invention seeks to discover the relationship between advanced glycosylation endproduct formation and amyloidosis. Prior to the instant invention, there has been no appreciation of a relationship between amyloidosis and advance glycosylation endproduct formation.

The citation of references herein shall not be construed as an admission that such is prior art to the present invention.

SUMMARY OF THE INVENTION

The present invention is broadly directed to the discoveries about the nature of AGE modification of amyloidogenic polypeptides, and the consequences of such modification for the pathology and therapeutic treatment of diseases or disorders associated with amyloidosis.

In particular, the inventors have discovered that AGE-amyloid polypeptides, in particular AGE-β amyloid peptide (βAP), facilitate further aggregation of amyloid polypeptides, whether such amyloid polypeptides are AGE-modified or not.

The inventors have further related this discovery to the enhanced ability of AGE-amylin polypeptides to facilitate aggregation of amylin (whether AGE-modified or not), resulting in amyloidosis of pancreatic tissue and death of pancreatic islet cells.

Thus, the invention relates to a method of modulating AGE-amyloid polypeptide-mediated amyloidosis in a mammal by controlling the formation of AGE-amyloid polypeptides. In a specific aspect of the invention, aggregation of βAP and amylin have been determined to be enhanced by the glycosylation reaction of βAP or amylin to form AGE-βAP or AGE-amylin as defined herein. Accordingly, the invention particularly extends to a method for modulating the in vivo aggregation of βAP and associated neurodegenerative amyloidosis by controlling the formation and presence of AGE-βAP. The invention further particularly extends to a method for modulating the in vivo aggregation of amylin and associated pancreatic islet cell amyloidosis by controlling formation and presence of AGE-amylin.

It has also been discovered that individuals suffering from an amyloidogenic disease have more AGEs associated with the amyloid polypeptides that form the amyloid plaques characteristic of the disease. The presence and level of AGE-amyloid polypeptides may reflect the total body burden of amyloid polypeptides and their age. In particular, patients with Alzheimer's disease have more AGEs associated with βAP than normal individuals of the same age, and patients with Type II diabetes may have more AGEs associated with amylin than normal individuals. Since the absolute levels of βAP in AD and normal individuals is about the same, the presence of AGE-βAP can be indicative or predictive of AD.

A corresponding diagnostic utility comprises the measurement of the course and extent of amyloidosis by a measurement of the presence and amount of AGE-amyloid polypeptides, and particularly AGE-βAP and AGE-amylin, as defined herein. An assay is included that may use the AGE-amyloid polypeptide of the present invention to identify disease states characterized by the presence of the AGE-amyloid polypeptide. Additionally, such an assay can be utilized to monitor therapy and thus adjust a dosage regimen for a given disease state characterized by the presence of the AGE-amyloid polypeptide. In specific embodiments, the diagnostic assays of the invention may be used to monitor the presence or level of AGE-βAP or AGE-amylin.

As noted above, AGE-amyloid polypeptide is useful as a marker of a variety of conditions in which the fluctuation in amyloid polypeptide levels may reflect the presence or onset of dysfunction or pathology. Moreover, AGE-amyloid polypeptide is useful alone and in conjunction with known carriers and delivery vehicles; such as liposomes, for the transport of therapeutic and other agents, including in certain instances the AGE moieties themselves, across membranes and epithelial layers, for example, and particularly the blood brain barrier, to particular sites in a patient for treatment. The particular site of interest may be an amyloid plaque that recognizes an AGE-amyloid polypeptide, such as the AGE-βAP, or AGE-amylin, or a portion thereof.

The presence of high levels of AGE-amyloid polypeptides in amyloidogenic diseases indicates that the normal clearance mechanisms for such polypeptides are faulty. Therefore, in a further aspect, the present invention provides compositions and methods for stimulating or inducing mechanisms of recognition and removal of AGE-amyloid in an animal, i.e., the invention contemplates activation of the scavenger system in an animal's body to remove the amyloid plaques. Such scavenger systems include the activity of phagocytic cells, e.g., macrophages and, in neural tissue, microglial cells.

Accordingly, the invention provides for stimulating or activating the natural scavenger systems by administration of stimulatory agents, including but not limited to, an advanced glycosylation endproduct, an AGE bound to a carrier, the fluorescent chromophore 2-(2-furoyl)-4(5)-(2-furanyl)-1H-imidazole (FFI) bound to a carrier, a monokine (e.g., lymphokine or cytokine) that stimulates phagocytic cells in the animal to increase the activity of recognizing and removing AGE-amyloid, and mixtures thereof. In a specific aspect, the AGE is an AGE-amyloid polypeptide.

Accordingly, the invention provides a method of preparing AGE-amyloid polypeptide, in particular AGE-βAP or AGE-amylin, which comprises incubation with an advanced glycosylation endproduct or a compound which forms advanced glycosylation endproducts for a length of time sufficient to form said AGE-amyloid polypeptide, e.g., AGE-βAP or AGE-amylin.

Pharmaceutical compositions are also disclosed that comprise an AGE-amyloid polypeptide in combination with a pharmaceutically acceptable carrier. Such pharmaceutical compositions may include an additional active agent(s) in some instances, and may be prepared and used for oral, parenteral or topical, e.g., transdermal, sublingual, buccal or transmucosal delivery. As stated, the pharmaceutical compositions can be in the form of a liposome in certain instances.

Generally, the therapeutic methods of the present invention contemplate the inhibition of in vivo amyloid aggregation by the administration of an agent or a pharmaceutical composition containing such agent or a plurality of such agents, for the inhibition of the formation of advanced glycosylation endproducts involving any or all of the amyloid polypeptide and amyloid precursor polypeptide, and materials subject to such in vivo aggregation. Such agents comprise antagonists of advanced glycosylation, and include antibodies to AGEs, antibodies to AGE-amyloid polypeptide, in particular AGE-βAP and AGE-amylin, as well as other ligands that would bind and neutralize the foregoing antigens. Suitable agents may also be selected from those agents that are reactive with an active carbonyl moiety on an early glycosylation product, and preferably are selected from aminoguanidine, a-hydrazinohistidine, analogs of aminoguanidine, and pharmaceutical compositions containing any of the foregoing, all as recited in detail herein. The invention set forth herein contemplates the discovery of additional agents that may then be used in like fashion and for like purpose.

Accordingly, it is a principal object of the present invention to modulate and control the in vivo aggregation of amyloid polypeptides leading to amyloidosis by controlling the formation of advanced glycosylation endproducts (AGEs), and particularly AGEs involving such amyloid polypeptides.

It is a further object of the present invention to provide a method for the prognosis, monitoring, and/or diagnosis of conditions in which abnormal amyloid accumulation is a characteristic, by detecting and measuring the presence and extent of AGE-amyloid polypeptide formation.

It is a still further object of the present invention to provide a method for diagnosing and treating diseases associated with amyloidosis. It is a particular object of the invention to provide a method for diagnosing, monitoring, and treating neurodegenerative diseases associated with amyloidosis, in particular Alzheimer's disease, by measuring and inhibiting the formation of AGE-βAP. It is another particular object to provide a method for diagnosing, monitoring, and treating diabetes Type II by measuring and inhibiting the formation of AGE-amylin.

It is a still further object of the present invention to provide a method for identifying new drugs and corresponding agents capable of treating abnormal amyloid polypeptide aggregation, in one aspect by use of an assay involving AGE-amyloid polypeptide, in particular AGE-βAP or AGE-amylin.

Still another object of the invention is to provide for removing amyloid plaques that have formed in a subject by activating the mechanisms for recognition and removal of AGE-amyloid in the body of a subject, and which may be directly or indirectly responsible for a pathology.

It is yet another object to utilize AGE-amyloid polypeptides, particularly AGE-βAP and AGE-amylin, to treat systemic or neurodegenerative diseases associated with amyloidosis, in particular Alzheimer's disease and Type II diabetes, respectively.

It is still a further object of the present invention to identify AGE-amyloid proteins and methods of inhibiting their formation in instances or disease conditions where the presence or biological activity of these AGE-amyloid proteins is detrimental to the host organism, or indicative of the presence of a disease state in the host organism.

Other objects and advantages will be apparent from a consideration of the ensuing detailed description which proceeds with reference to the following illustrative drawings.

BRIEF DESCRIPTION OF THE DRAWINGS

FIG. 5 presents data showing that amyloid plaque-enriched fractions of Alzheimer's diseased pre-frontal cortex contain more AGE adducts per mg protein than equivalently prepared fractions of age-matched, non-demented controls. Each control patient is represented by a circle and AD patients by triangles. Each symbol represents the average of at least 4 independent measurements of immunoreactive AGE adducts for each patient sample with the mean of each patient group marked by a cross symbol.

DETAILED DESCRIPTION OF THE INVENTION

Figure 1:
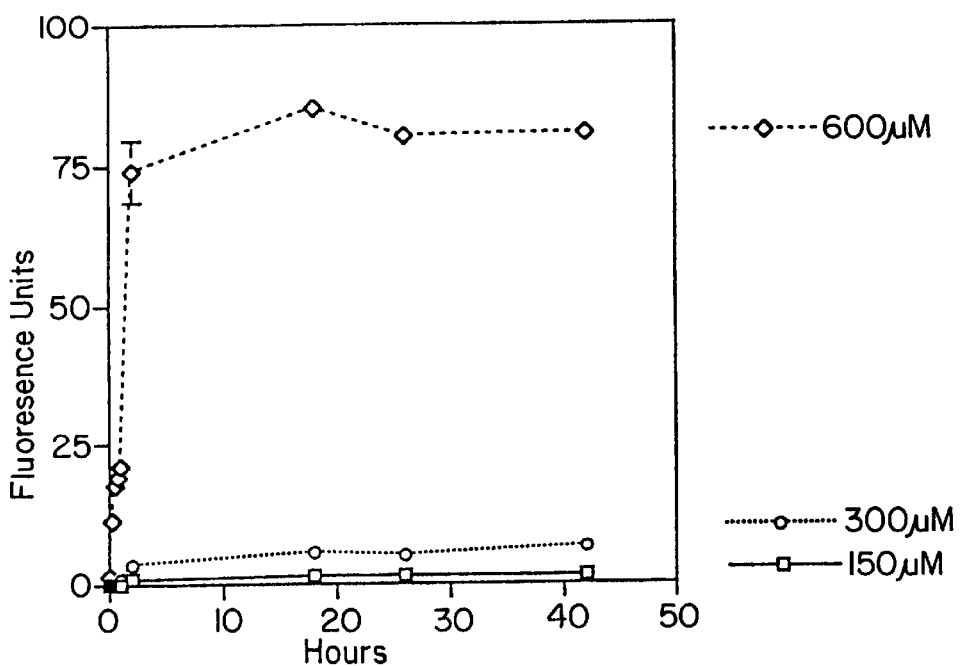
FIG. 1 presents a graph demonstrating that fluorescent aggregates formed with synthetic βAP depend on initial concentration of soluble polypeptide and time. Synthetic βAP 1–28 was incubated with 0.1 M sodium acetate, pH 7.2. Aliquots were removed at different times for measurement of fluorescence in the presence of Thioflavin-T. The mean of 3 measurements ±standard error is plotted for 600 $\mu$M (diamonds), 300 $\mu$M (circles) and 150 $\mu$M (squares) concentrations of βAP.

The present invention relates to the prevention and treatment of a degenerative systemic, local, or neurological disease associated with amyloidosis.

In one aspect, the invention provides compositions and methods to prevent the formation or cross-linking of AGE-modified proteins involved in amyloidosis. In a particular embodiment, the invention relates to the prevention of amyloidosis of the β-amyloid peptide (βAP) by inhibiting the formation of advanced glycosylation endproduct (AGE)-modified βAP. βAP is a component of the amyloid plaques associated with Alzheimer's disease (AD), as well as other amyloidogenic degenerative neurological diseases. In another embodiment, the invention relates to the prevention of arnyloidosis of amylin by inhibiting the formation of advanced glycosylation endproduct (AGE)-modified amylin. Amylin is a component of the amyloid fibrils found with pancreatic islet cells in association with Type II diabetes. In other embodiments, the invention relates to AGE-modulated amyloidosis of immunoglobulins produced by multiple myeloma, amyloidosis associated with serum amyloid A peptide, and amyloidosis of the protein associated with one of the various spongiformn encephalopathies, i.e., prion protein (PrP) or scrapie-associated fibril (SAF) protein.

In another aspect, the invention provides for clearance of amyloid plaques by activating resident phagocytic cells that express AGE receptors, increasing the AGE content of the plaque, or both.

The invention is based, in part, on the discovery that the level of AGE found in brain samples from AD patients is significantly greater than in similarly prepared samples from age-matched control subjects. Additional evidence forming a basis, in part, for the invention is the observation that AGE epitopes are located in amyloid plaques in hamster-adapted murine scrapie, a form of spongiformn encephalopathy. The invention is further based partially on experiments demonstrating that AGE-modification of βAP enhances the efficiency of βAP aggregation, and that an inhibitor of AGE formation, in particular, aminoguanidine (AG), can inhibit the AGE-enhanced aggregation of 3AP.

Numerous abbreviations and terms are used herein to simplify the terminology used, and to facilitate a better understanding of the invention.

The terms "amyloid," "amyloid plaque," and "amyloid fibril" refer generally to insoluble proteinaceous substances with particular physical characteristics independent of the composition of proteins or other molecules that are found in the substance. Amyloid can be identified by its amorphous structure, eosinophilic staining, and homogeneous appearance. Protein or peptide components of amyloid are termed herein "amyloid polypeptides," and include, but are not limited to, βAP; scrapie protein precursor or prion protein; immunoglobulin, including κ or λ light or heavy chains, or fragments thereof, produced by myelomas; serum amyloid A; $β_2$-microglobulin; apoA1; gelsolin; cystatin C; (pro) calcitonin; atrial natururetic factor; islet amyloid polypeptide, also known as amylin (see, Westermark et al., 1987, Proc. Natl. Acad. Sci. USA 84:3881–85; Westermark et al., 1987, Am. J. Physiol. 127:414–417; Cooper et al., 1987, Proc. Natl. Acad. Sci. USA 84:8628–32; Cooper et al., 1988, Proc. Natl. Acad. Sci. USA 85:7763–66; Amiel, 1993, Lancet 341:1249–50); and the like. It should be noted that human and cat amylin are amyloidogenic peptides, and aggregate spontaneously in vitro to form insoluble fibrils, whereas rat amylin, which differs from human amylin at six amino acid residues, is non-amyloidogenic and does not form fibrils (see, Lorenzo et al., 1994, Nature 368:756–760). In a specific aspect, the term "amyloid" is used herein to refer to substances that contain βAP, scrapie protein, or amylin. "Amyloidosis" refers to the in vivo deposition or aggregation of proteins to form amyloid plaques or fibrils.

As used herein, the term "AGE-" refers to the compound which it modifies as the reaction product of either an advanced glycosylation endproduct or a compound which forms AGEs and the compound so modified, such as the βAP or amylin moiety. AGE-amyloid polypeptide can be formed in vitro or in vivo by reacting an amyloidogenic polypeptide or amyloid as defined herein with an AGE, such as AGE-βAP or AGE-amylin, or with a compound such as a reducing sugar, e.g., glucose, until the peptide is modified to form the AGE-peptide.

The term "glycosylation" is used herein to refer to the non-enzymatic reaction of reducing sugars with a nucleophile, in particular an amine group, on an amyloid polypeptide, such as βAP, which leads to formation of AGEs. These processes are well known in the art, as described above. An alternative term for this process that has come more frequently into use is "glycation."

A molecule is "antigenic" when it is capable of specifically interacting with an antigen recognition molecule of the immune system, such as an immunoglobulin (antibody) or T cell antigen receptor. An antigenic peptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a larger, immunogenic carrier molecule for immunization. A molecule that is antigenic need not be itself immunogenic, i.e., capable of eliciting an immune response without coupling to such a carrier.

A composition comprising "A" (where "A" is a single protein or polypeptide, DNA molecule, vector, recombinant host cell, etc.) is substantially free of "B" (where "B" comprises one or more contaminating proteins or polypeptides, DNA molecules, vectors, etc.) when at least about 75% by weight of the proteins or polypeptides, DNA, vectors (depending on the category of species to which A and B belong) in the composition is "A". Preferably, "A" comprises at least about 90% by weight of the A+B species in the composition, most preferably at least about 99% by weight. It is also preferred that a composition be substantially free of contamination, and generally that such compositions contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" in this context refers to a diluent, adjuvant, excipient, or vehicle with which the compound is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as BCG (bacille Calmette-Guerin) and *Corynebacterium parvum*. Preferably, the adjuvant is pharmaceutically acceptable.

A disease or disorder is associated with amyloidosis when amyloid deposits or amyloid plaques are found in or in proximity to tissues affected by the disease, or when the disease is characterized by overproduction of a protein that is or can become insoluble. The amyloid plaques may provoke pathological effects directly or indirectly by known or unknown mechanisms. Examples of amyloid diseases include, but are not limited to, systemic diseases, such as chronic inflammatory illnesses, multiple myeloma, macroglobulinernia, familial amyloid polyneuropathy (Portuguese) and cardiomyopathy (Danish), systemic senile amyloidosis, familial amyloid polynephropathy (Iowa), familial amyloidosis (Finnish), Gerstmann-Straussler-Scheinker syndrome, familial amyloid nephropathy with urticaria and deafness (Muckle-Wells syndrome), medullary carcinoma of thyroid, isolated atrial amyloid, and hemodialysis-associated amyloidosis (HAA); and neurodegenerative diseases.

Type II diabetes is associated with amyloid fibrils or deposits of the pancreas, in particular the islet cells that produce insulin. As with Alzheimer's disease amyloid plaques, the amyloid plaques or fibrils provoke pathological effects. In particular, concentrations of human amylin at which fibrils form are toxic for human and rat pancreatic islet insulin-producing fl-cells (Lorenzo et al., 1994, Nature 368:758–760). Accordingly, in a specific embodiment, the invention relates to Type II diabetic amyloidosis.

Chronic inflammatory illnesses, such as idiopathic familial Mediterranean fever, Muckle-Wells syndrome, chronic malarial infection, and the like, can result in expression of serum amyloid A, an acute phase protein which may undergo further processing and form amyloid deposits and plaques. For example, in the Third World, chronic malaria can lead to amyloidosis of the spleen and/or liver of an individual. The resulting organ failure can ultimately lead to death. Multiple myeloma is associated with overproduction of immunoglobulins, which immunoglobulins or fragments thereof can form amyloid deposits and plaques in organs or tissues in contact with the circulatory system. Deposition of transthyretin can result in familial amyloid polyneuropathy (Portuguese), familial amyloid cardiomyopathy (Danish), or systemic senile amyloidosis. Hemodialysis-associated amyloidosis is a complication among long-term hemodialysis patients, in which $\beta_2$-microglobulin is a major protein constituent of the amyloid fibrils (Drueke, 1991, Miner. Electroyte Metab. 17:261–272; Geyjo et al., 1985, Biochem. Biophys. Res. Commun. 129:701–706; Gorevic et al., 1986, Proc. Natl. Acad. Sci. USA 83:7908–12; Shirahama et al., 1985, Lab. Invest. 53:705–709).

As noted above, in addition to systemic amyloidosis, the present invention relates particularly to neurodegenerative diseases involving amyloidosis. The term "neurodegenerative disease" refers to a disease or disorder of the nervous system, particularly involving the brain, that manifests with symptoms characteristic of brain or nerve dysfunction, e.g., short-term or long-term memory lapse or defects, dementia, cognition defects, balance and coordination problems, and emotional and behavioral deficiencies. Such diseases are "associated with amyloidosis" when histopathological (biopsy) samples of brain tissue from subjects who demonstrate such symptoms would reveal amyloid plaque formation. As biopsy samples from brain, especially human brain, are obtained with great difficulty from living subjects or might not be available at all, often the association of a symptom or symptoms of neurodegenerative disease with amyloidosis is based on criteria other than the presence of amyloid deposits, such as plaques or fibrils, in a biopsy sample.

In a specific embodiment, according to the present invention the neurodegenerative disease associated with amyloidosis is Alzheimer's disease (AD). In other embodiments, the disease may be the rare Swedish disease characterized by a double KM to NL mutation in amyloid precursor protein (APP) near the amino-terminus of the βAP portion of APP (Levy et al., 1990, Science 248:1124–26). Another such disease is hereditary cerebral hemorrhage with amyloidosis (HCHA or HCHWA)-Dutch type (Rozemuller et al., 1993, Am. J. Pathol. 142:1449–57; Roos et al., 1991, Ann. N.Y. Acad. Sci. 640:155–60; Timmers et al., 1990, Neurosci. Lett. 118:223–6; Haan et al., 1990, Arch. Neurol. 47:965–7). Other such diseases known in the art and within the scope of the present invention include, but are not limited to, sporadic cerebral amyloid angiopathy, hereditary cerebral amyloid angiopathy, Down's syndrome, Parkinson-dementia of Guam, and age-related asymptomatic amyloid angiopathy (see, e.g., Haan and Roos, 1990, Clin. Neurol. Neurosurg. 92:305–310; Glenner and Murphy, 1989, N.

Neurol. Sci. 94:1–28; Frangione, 1989, Ann. Med. 21:69–72; Haan et al, 1992, Clin. Neuro. Neurosurg. 94:317–8; Fraser et al., 1992, Biochem. 31:10716–23; Coria et al., 1988, Lab. Invest. 58:454–8). The actual amino acid composition and size of the βAP involved in each of these diseases may vary, as is known in the art (see above, and Wisniewski et al., 1991, Biochem. Biophys. Res. Commun. 179:1247–54 and 1991, Biochem. Biophys. Res. Commun. 180:1528 [published erratum]; Prelli et al., 1990, Biochem. Biophys. Res. Commun. 170:301–307; Levy et al., 1990, Science 248:1124–26).

In a further aspect, the neurodegenerative disease is a subacute spongiform encephalopathy, such as but not limited to, scrapie, Creutzfeldt-Jakob disease, Gerstmann-Straussler disease, kuru, chronic wasting disease of mule-deer and elk, bovine spongiform encephalopathy of cattle, and mink transmissible encephalopathy.

The instant invention contemplates the treatment of animals, and more preferably, mammals, including humans, as well as mammals such as dogs, cats, horses, cows, pigs, guinea pigs, mice and rats.

Treatment of Neurodegenerative Amyloidosis by Inhibiting AGE

In one aspect, the present invention provides for therapeutic treatment for the prevention or inhibition of amyloidosis associated with diseases or disorders, e.g., neurodegenerative diseases, in particular Alzheimer's disease. In broad aspect, the therapeutic method of the invention involves administration of an agent that is capable of controlling the production, formation, or accumulation of advanced glycosylation endproducts. Such agents include, but are not limited to, antibodies against advanced glycosylation endproducts, ligands, including AGE receptors and active fragments thereof, capable of binding to and neutralizing advanced glycosylation endproducts, and compounds capable of inhibiting the formation of advanced glycosylation endproducts. In particular, the invention relates to an inhibitor of glycosylation, preferably an inhibitor of AGE formation, to the brain of a subject believed to be in need of such treatment. Such an agent is termed herein "capable of inhibiting the formation of AGEs", or alternatively an "inhibitor of AGE formation", "inhibitor of advanced glycosylation," or an "agent that inhibits advanced glycosylation."

The present invention further contemplates a dual therapeutic strategy, where agents that inhibit advanced glycosylation, such as aminoguanidine, may be administered to inhibit in vivo AGE-amyloid polypeptide formation and consequent initiation of amyloid polypeptide aggregation, plaque formation, and amyloidosis; and to react with any byproducts of an ongoing amyloid glycosylation to prevent reaction of these byproducts with proteins, particularly other amyloid polypeptides, resulting in proteolytically resistant cross-links in the amyloid plaque.

The therapeutic (and, as discussed below, the diagnostic) methods of the present invention contemplate the use of agents that have an impact on the formation of AGE-amyloid. Among these agents, antibodies to AGEs and other ligands may be prepared and used.

The rationale of the invention is to use agents which block the post-glycosylation step, i.e., the formation of fluorescent chromophores and/or molecular crosslinks whose presence is associated with, and leads to, the adverse sequelae of glycosylation. An ideal agent would prevent the formation of AGE-associated chromophores and/or cross-links bridging proteins and covalently trapping proteins onto other proteins, such as occurs in amyloid plaques.

The present invention does not attempt to prevent initial protein glycosylation reactions, as it would be nearly impossible to use agents which prevent the reaction of glucose with protein amino groups. The agents that are capable of preventing initial glycosylation are likely to be highly toxic, and since the initial glycosylation comes to equilibrium in about three weeks, there is inadequate time available to achieve this objective. Instead, the ideal agent would prevent or inhibit the long-term, post-glycosylation steps that lead to the formation of the ultimate advanced glycosylation end products that are a direct cause of the pathology associated with amyloidosis.

In a further aspect of the invention, an inhibitor of the formation of AGEs includes compounds that react with a carbonyl moiety of an early glycosylation product. Representative of such advanced glycosylation inhibitors are aminoguanidine, lysine and α-hydrazinohistidine. In a specific embodiment, the inhibitor is aminoguanidine (AG) and derivatives thereof. Pharmaceutical compositions and methods involving AG and derivatives thereof are well known, as described in U.S. Pat. No. 4,758,583, issued Jul. 19, 1988; U.S. Pat. No. 4,908,446, issued Mar. 13, 1990; U.S. Pat. No. 4,983,604, issued Jan. 8, 1991; U.S. Pat. No. 5,100,919, issued Mar. 31, 1992; U.S. Pat. No. 5,106,877, issued Apr. 21, 1992; U.S. Pat. No. 5,114,943, issued May 19, 1992; U.S. Pat. No. 5,128,360, issued Jul. 7, 1992; U.S. Pat. No. 5,130,324, issued Jul. 14, 1992; U.S. Pat. No. 5,130,337, issued Jul. 14, 1992; U.S. Pat. No. 5,137,916, issued Aug. 11, 1992; U.S. Pat. No. 5,140,048, issued Aug. 18, 1992; U.S. Pat. No. 5,175,192, issued Dec. 29, 1992; U.S. Pat. No. 5,218,001, issued Jun. 8, 1993; U.S. Pat. No. 5,221,683, issued Jun. 22, 1993; U.S. Pat. No. 5,238,963, issued Aug. 24, 1993; U.S. Pat. No. 5,243,071, issued Sep. 7, 1993; and U.S. Pat. No. 5,254,593, issued Oct. 19, 1993. Other inhibitors of AGE formation are described in U.S. applications Ser. No. 07/652,575, filed Feb. 8, 1991; Ser. No. 07/889,141, filed May 27, 1992; Ser. No. 07/896,854, filed May 15, 1992; Ser. No. 07/986,661, filed Dec. 8, 1992; Ser. No. 07/986,662, filed Dec. 8, 1992; Ser. No. 08/027,086, filed Mar. 5, 1993; and Ser. No. 08/095,095, filed Jul. 20, 1993. Each of the foregoing patents and patent applications is specifically incorporated herein by reference in its entirety. Such inhibitors of AGE formation can be administered directly to the brain or cerebrospinal fluid, e.g., by direct cranial or intraventricular injection, or may pass through the blood brain barrier following administration by parenteral injection, oral administration, skin absorption, etc.

Accordingly, such compounds include a variety of hydrazine derivatives having, for example, a generic formula as follows:

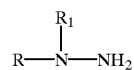

wherein R is a group of the formula

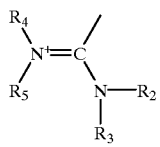

and $R_1$ is hydrogen or a lower alkyl group of 1–6 carbon atoms, a hydroxyethyl group, or together with $R_2$ may be a lower alkylene bridge of 2–4 carbon atoms; $R_2$ is hydrogen or a lower group alkyl of 1–6 carbon atoms or together with $R_1$ or $R_3$ is a lower alkylene bridge of 2–4 carbon atoms, amino, hydroxy, or an aminoalkylene group of the formula

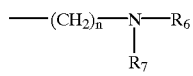

wherein n is an integer of 2–7 and $R_6$ and $R_7$ are independently a lower alkyl group of 1–6 carbon atoms or together form a part of a cycloalkyl or heterocyclic ring containing from 1 to 2 heteroatoms, of which at least one is nitrogen; and the second of said heteroatoms is selected from the group consisting of nitrogen, oxygen, and sulfur; with the proviso that when the second of said heteroatoms of the heterocyclic ring is nitrogen and forms a piperazine ring; it may be optionally substituted by a substituent that is identical to the portion of the compound on the first nitrogen of the piperazine ring; $R_3$ is hydrogen, a lower alkyl group of 1–6 carbon atoms, or together with $R_2$ or $R_4$ is a lower alkylene bridge of 2–4 carbon atoms; $R_4$ is hydrogen, a lower alkyl group of 1–6 carbon atoms or together with $R_3$ is a lower alkylene bridge of 2–4 carbon atoms; or an amino group; $R_5$ is hydrogen, or a lower alkyl group of 1–6 carbon atoms; with the proviso that at least one of $R_1$, $R_2$, $R_3$, $R_4$ or $R_5$ is other than hydrogen; or R is an acyl or a lower alkylsulfonyl group of up to 10 carbon atoms and $R_1$ is hydrogen; and their pharmaceutically acceptable acid addition salts.

In a particular aspect, where the disease associated with amyloidosis is a neurodegenerative disease, preferably an inhibitor of AGE formation may be capable of crossing the blood brain barrier. The blood brain barrier of subjects suffering from brain amyloidosis is often found in deteriorated condition, and this facilitates the ability of agents administered parenterally to traverse the barrier. In another embodiment, the inhibitor of AGE formation can be conjugated with a targeting molecule, such as transferrin, for which there are receptors on the blood brain barrier. In a further embodiment, the inhibitor can be modified to have decreased polarity, or increased hydrophobicity, as more hydrophobic (less polar) agents cross the blood brain barrier more readily. In a further embodiment, hydrophobic (nonpolar) inhibitors of AGE formation can be selected and used. In yet another embodiment, the inhibitor of advanced glycosylation can be administered in a liposome, particularly a liposome targeted to the blood brain barrier. Administration of pharmaceutical agents in liposomes is known (see Langer, 1990, Science 249:1527–1533; Treat et al., in *Liposomes in the Therapy of Infectious Disease and Cancer*, Lopez-Berestein and Fidler (eds.), Liss, New York, pp. 353–365 (1989); Lopez-Berestein, ibid., pp. 317–327; see generally ibid.).

These and other strategies for directing therapeutic agents across the blood brain barrier are known in the art, and contemplated by the present invention.

In another embodiment, inhibitors of AGE can be antibodies. Antibodies can bind to and inactivate or mediate clearance of AGE-modified amyloid polypeptides. In one aspect of the invention, the antibody described in Makita et al. (1992, J. Biol. Chem. 267:5133–38) can be used. The invention further provides for generation of antibodies to AGE epitopes of AGE-amyloid polypeptides. Such antibodies can be prepared using techniques well known in the art. Preferably, the immunogen used to prepare the antibodies is an AGE-amyloid protein. In a specific aspect, AGE-βAP can be used. In another embodiment, AGE-amylin can be used.

The AGE-βAP or AGE-amylin may be used to produce antibody(ies) to themselves. Such antibodies can be produced and isolated by standard methods including the well known hybridoma techniques. Generally, antibodies can be produced by immunization of an animal with AGE-βAP or AGE-amylin, free or conjugated with a carrier protein, such as but not limited to keyhole limpet hemocyanin (KLH) or BSA, preferably admixed with an adjuvant as defined above.

The term "antibody" includes any immunoglobulin, including antibodies and fragments thereof that binds a specific epitope, and such general definition is intended to apply herein. The term therefore encompasses polyclonal, monoclonal and chimeric antibodies, the last mentioned described in further detail in U.S. Pat. Nos. 4,816,397 and 4,816,567. Also, an "antibody combining site" is that structural portion of an antibody molecule comprised of heavy and light chain variable and hypervariable regions that specifically bind antigen.

Exemplary antibodies include antibody molecules such as intact immunoglobulin molecules, substantially intact immunoglobulin molecules and those portions of an immunoglobulin molecule that contain the active binding site, including those portions known in the art as Fab, Fab', $F(ab')_2$ and F(v), which portions are preferred for use in therapeutic methods associated herein.

Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from $F(ab')_2$ portions by reduction of the disulfide bonds linking the two heavy chain portions as with mercaptoethanol, and followed by alkylation of the resulting protein mercaptan with a reagent such as iodoacetamide.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. An antibody may be.prepared having a plurality of antibody combining sites, each immunospecific for a different antigen, e.g., a bispecific (chimeric) antibody.

While intravenous injection is a very effective form of parenteral administration, other modes can be employed, including but not limited to intraventricular, intramuscular, intraperitoneal, intra-arteriolar, and subcutaneous injection as well as oral, nasal and topical administration. Intraventricular injection may be preferred for treatment of a neurodegenerative disease. Intravenous injection may be preferred for systemic amyloidosis, or for treating amyloidosis associated with Type II diabetes.

Preferably, the treatment is effected prophylactically, to prevent the initial formation of amyloid seed, which may facilitate aggregation of non-AGE modified amyloid polypeptide, such as soluble βAP or soluble amylin, as well as AGE-amyloid polypeptide. In a particular embodiment, an inhibitor of AGE formation that can traverse the blood brain barrier, as described above, can be administered to a subject believed to be at increased risk for Alzheimer's disease or another neurodegenerative disease that involves amyloidosis to inhibit the onset or progression of the disease at an early stage. In another embodiment, the inhibitor of AGE formation can be injected intraperitoneally or intravenously in a subject believed to be at increase risk for Type II diabetes, e.g., a person suffering from obesity or one of the other conditions associated with Type II diabetes. For example, subjects that have a genetic predisposition to AD or Type II diabetes can be treated prophylactically. The actual dosage and treatment regimen for such prophylaxis can be readily determined by the ordinary skilled physician, taking into account the route of administration, age and weight of the patient, and the particular disease state for which the patient is undergoing treatment, as well as the stage thereof, and, of course, any side effects of the inhibitor, efficacy of the inhibitor, in accordance with customary medical procedures and practices.

The invention further contemplates that the inhibitors of AGE-formation can be administered in conjunction with other therapies for the treatment of diseases that involve amyloidosis. For example, for treatment of a neurodegenerative disease, in particular Alzheimer's disease, an inhibitor of AGE-formation can be administered in conjunction with a therapy designed to inhibit production of βAP, such as those described by Gandy et al., U.S. Pat. No. 5,242,932, issued Sep. 7, 1993; Wagner et al., International Patent Publication No. WO 93/09233, published May 13, 1993; and Buxbaum et al., European Patent Publication No. 0457295 A2, published 21 November 1991. In another example, for treatment of Type II diabetes, administration of an inhibitor of AGE-formation can be effected in conjunction with administration of one or more of sulfonylureas (drugs to increase the level of insulin production), insulin, hypertension medication, and imposition of a diet and exercise regimen.

Treatment of Amyloidosis by Increasing AGE Clearance

In accordance with the present invention, a method and associated agents are disclosed for the inhibition and treatment of amyloidosis in animals by stimulating the bodies of such animals to increase their recognition of and affinity for advanced glycosylation endproducts. In particular, phagocytic cells such as monocytes, macrophages and/or microglial cells are treated with an agent capable of causing the phagocytic cells to increase their activity of recognizing and removing AGE-modified amyloid plaques.

The agents of the present invention comprise one or more stimulator compounds in turn, comprising a natural or synthetic advanced glycosylation endproduct alone or bound to a carrier, said carrier including a material selected from carbohydrates, proteins, synthetic polypeptides, lipids, biocompatible natural and synthetic resins, antigens, and mixtures thereof. The stimulator compounds could include other advanced glycosylation endproducts that may be prepared from the reaction between sugars and other macromolecules, and monokines which stimulate phagocytic cells to increase their activity toward advanced glycosylation endproducts (see. U.S. Pat. No. 4,900,747, issued Feb. 13, 1990 to Vlassara et al., which is incorporated herein by reference in its entirety).

Accordingly, the stimulator compound may comprise the compound FFI bound to a protein such as albumin. Alternately, the stimulator compound may comprise a synthetically derived advanced glycosylation endproduct which is prepared, for example, by the reaction of glucose or glucose-6-phosphate with albumin. This reaction product can be used alone or with a carrier in the same fashion as the FFI-albumin complex. In a specific aspect, the stimulator compound is an AGE-amyloid polypeptide.

A monokine that functions as a stimulator compound comprises the protein known as Tumor Necrosis Factor (TNF) discovered and isolated by one of the inventors herein and named "cachectin." This material may be administered alone or in conjunction with other stimulator compounds.

In addition, the stimulator compounds of the present invention may be administered in conjunction with materials identified hereinafter as "co-stimulatory agents." The co-administration of the stimulator compound with the co-stimulatory agents has been found to potentiate the activity of the former. Suitable co-stimulatory agents include monokines such as Interleukin-1 (IL-1) and gamma-interferon.

A further alternative embodiment of the method of the present invention and one which may be practiced independently or conjointly with the above recited method, is the ex vivo treatment of the phagocytic cells to expose them to the stimulator compounds. For example, a patient may be given an extracorporeal blood treatment in which blood is diverted out of the body from the arterial and venous system and is directed through a device which contains stimulator compounds and/or co-stimulatory agents which are suitably positioned to come in contact with the phagocytic cells within the blood. The stimulator compounds and/or co-stimulatory agents may be immobilized or may be allowed to enter the flow of the body fluid.

In the instance where the method comprises the in vivo administration of the stimulator compound and/or stimulatory agents, such administration may be accomplished by known techniques, including oral techniques and parenteral techniques such as intradermal, subcutaneous, intravenous, or intraperitoneal injection, catheterization or other conventional means. The stimulator compounds or mixtures of them may be prepared in suitable pharmaceutical compositions for such administration.

In a specific embodiment, AGE-modified amyloid polypeptides are useful for activating tissue phagocytic cells, such as macrophages, which can in turn metabolize amyloid deposits or plaques. Such an amyloid polypeptide may have an amino sequence identical to the native amino acid sequence, or it may be modified to include one or more additional sites for non-enzymatic glycation and AGE formation. For example, a histidine, asparagine, or glutamine residue (i.e., a polar or cationic residue) may be substituted with lysine.

As noted above, administration of an AGE-modified amyloid polypeptide can activate phagocytic mechanisms in tissue phagocytic cells. In addition to phagocytosing amyloid, such phagocytic cells may also secrete enzymes that help degrade amyloid, and may recruit other cells that can assist in the removal of amyloid.

In a further particular aspect, the AGE-βAP or other AGE-neural amyloid polypeptides of this invention can be utilized as stimulants of activation of neural phagocytic cells, in particular microglia, to activate the microglia to effect removal of AGEs and/or AGE-modified polypeptides, and thus, amyloid. Such phagocytic cells are capable of recognizing and removing abnormal macromolecules by means of receptors on their surfaces which recognize specific chemical structures and bind them. Once the abnormal macromolecule is recognized in this way, the phagocytic cell may internalize the macromolecule and may then degrade it. In some instances, the phagocytic cell may in addition secrete enzymes and other factors to help degrade the molecule or particle extracellularly if it cannot be internalized or to induce other cells to participate in such degradation. After the amyloid is removed, normal function of the affected area may resume.

In another specific aspect, the invention contemplates administration of AGE-amylin to activate the body's absorption mechanisms to remove pancreatic amyloid plaques or fibrils associated with Type II diabetes.

The present invention contemplates that the phagocytic cells can be activated by exposure to stimulator compounds that potentiate the capability of these cells with respect to their recognition and affinity for, and capability to degrade, advanced glycosylation end products. In particular, the exposure of these cells to certain stimulator compounds has been found to increase the number of receptors developed on these cells and to thereby increase the capacity and efficiency of these cells with respect to the recognition and degradation of advanced glycosylation endproducts. Thus, in a specific aspect, the AGE-βAP or AGE-amylin of the present invention can function as a stimulator compound, as can other compounds known to stimulate phagocyte-mediated AGE-specific activity (see U.S. Pat. No. 4,665,192, issued May 12, 1987 and U.S. Pat. No. 4,900,747, issued Feb. 13, 1990, and copending U.S. application Ser. No. 07/878,837, filed May 5, 1992).

Accordingly, the method of the present invention generally comprises exposing brain tissue to AGE-amyloid polypeptide, or exposing pancreatic tissue to AGE-amylin, which can result in activation of the mechanisms for an increase in the recognition and removal of amyloid that has undergone advanced glycosylation.

In a further embodiment, where a subject presently manifests the symptoms of a disease associated with amyloidosis as described above, particularly involving dementia in neurodegeneration or adult onset diabetes, the present invention contemplates modifying the amyloid plaques to increase the level of AGEs, so as to increase the availability of the plaques as targets for degradation by the pathways of recognition and removal of AGE-modified molecules, in particular by activation of phagocytic cells. For example, amyloid targeting agents, like Congo Red and Thioflavin (see Caughey et al., U.S. Pat. No. 5,276,059, issued Jan. 4, 1994, which is hereby incorporated by reference in its entirety), including derivatives and analogs thereof that demonstrate affinity for binding amyloid, can be modified to bear AGEs or AGE precursors (hereinafter, both AGE and AGE precursor modified targeting agents are termed "AGE" modified targeting agents) and administered so as to target said AGEs or AGE precursors to amyloid deposits. The structures of Thioflavin T and Congo Red are shown below:

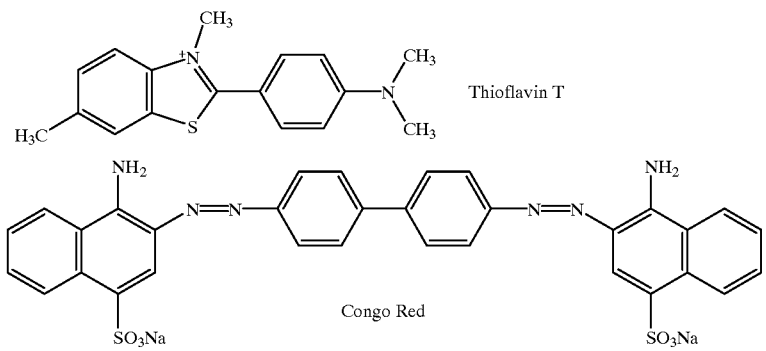

The AGE-amyloid targeting agents of the invention can be administered via any route, e.g., i.v., i.p., i.m., intraventricularly, intracranially, orally, nasally, through a skin patch, etc. In a specific aspect, these agents are modified to be capable of crossing the blood brain barrier, and thus modified, are attractive candidates for increasing the level of AGEs on amyloid plaques associated with neurodegenerative disease.

Any AGE or AGE precursor, such as an Amadori compound, can be conjugated to the amyloid targeting agent for use in increasing the level of AGE modification of amyloid. Examples of such AGEs or AGE precursors include, but are not limited to, FFI, fructopyranose and derivatives thereof, and the like. In specific embodiments, infra, Thioflavin is conjugated with an Amadori compound, such as 6-amino(1-deoxy-β-D-fructopyranos-1-yl) and 6-N,N-dimethylamino(1-deoxy-β-D-fructopyranos-1-yl) groups as shown in an Example, infra, to form AGE-Thioflavin (AGE-TF). In another embodiment, Congo Red is conjugated with an Amadori compound, e.g., as outlined in Scheme I, as follows:

Scheme I
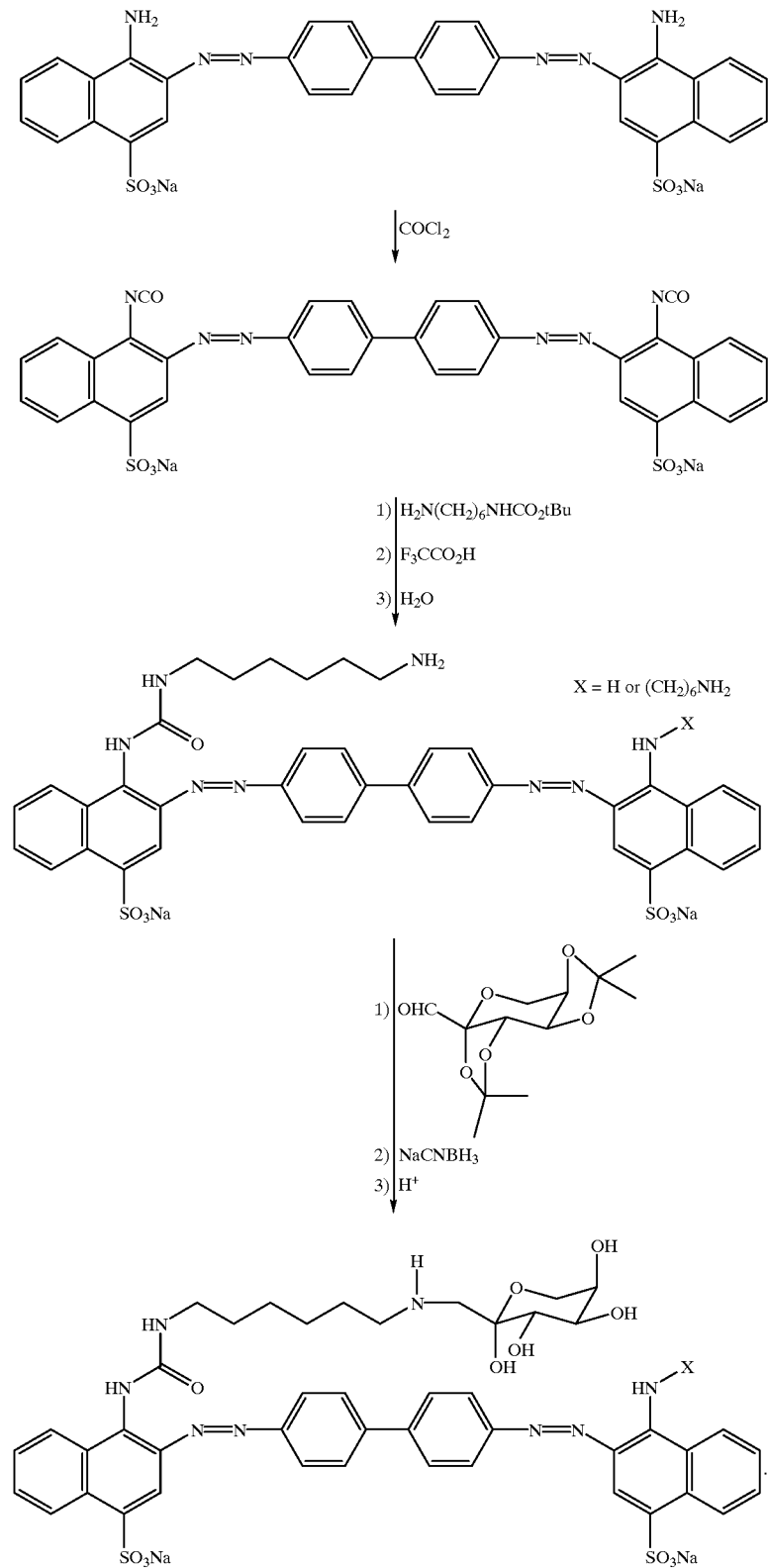

-continued

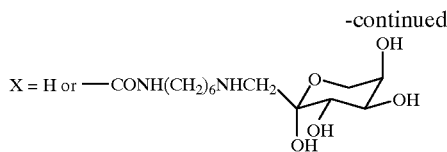

The Thioflavin or Congo Red moiety targets the Amadori compound to amyloid plaques and fibrils, in order to induce AGE formation mediated by the Amadori product on or in immediate association with the amyloid plaque or fibril, resulting in formation of AGE-modified amyloid, thus increasing the likelihood of uptake of the amyloid plaque or fibril by local or recruited phagocytic cells.

In a specific embodiment, AGE-TF can be administered to an individual with AD in order to induce AGE formation in the βAP-amyloid plaques associated with AD. Increased levels of AGE modification of the amyloid increases the likelihood of uptake by central nervous system microglia or recruited peripheral monocytes, or both, and facilitates removal of the amyloid.

In another specific embodiment, AGE-TF or AGE-Congo Red can be administered to an individual with Type II diabetes to induce AGE formation of the amylin-amyloid plaques associated with Type II diabetes. Increased levels of AGE modification of the amyloid increases the likelihood of uptake by local or recruited phagocytic cells, and facilitates removal of the amyloid.

The effectiveness of an AGE bearing targeting agent, such as AGE-TF or AGE-Congo Red, can be tested in vitro and in vivo for efficacy at AGE modification of amyloid. This AGE modification may be non-covalent through the association of the targeting agent and amyloid, or covalent due to the inherent reactivity of the AGE or AGE precursor for sites on the amyloid. In the following examples, the amyloid polypeptide flAP and the amyloid targeting agent Thioflavin (TF) are described for convenience. However, the present disclosure contemplates performance of the same or similar assays with any amyloid model system and any amyloid-specific targeting agent, and is not intended to be limited to the following examples.

An in vitro assay can be used to determine the ability of AGE-TF to AGE modify insoluble or aggregated βAP or amylin. For example, AGE-TF can be incubated with insoluble βAP or insoluble amylin to produce AGE-modified insoluble or aggregated βAP or amylin. The level of AGE modification can be determined, e.g., by ELISA using an anti-AGE antibody, and compared to a control treated with the unmodified Thioflavin. Further testing for clearance of the AGE-modified insoluble βAP can be conducted by incubation with cultured phagocytic cells, such as mouse peritoneal macrophages, elicited macrophages, the RAW 264.7 cell line, human peripheral monocytes, or inicroglia or astroglia primary cells or cell lines.

Involvement of AGE-receptor-mediated uptake by phagocytic cells can be evaluated with a standard binding assay. Insoluble or aggregated labelled βAP (e.g., $^{125}$I-βAP, although any labelling means known in the art, such as are discussed below, can be used) is contacted with an AGE-TF or TF alone (control), and incubated with about 106 cells per well in the presence of increasing concentrations of cold AGE-BSA as a standard competitor. The amount of labelled βAP or amylin bound in the absence of competing AGE-BSA is then compared to the amount in the presence of different concentrations of AGE-BSA. Standard methods can then be used to derive the number, affinity and association kinetics of AGE-modified amyloid binding sites on the cells. Labelling of the βAP or amylin should precede AGE modification by AGE-TF treatment to ensure that the βAP or amylin is the labelled moiety. Additional controls can include untreated βAP or amylin alone.

An uptake assay can also be performed. In the uptake assay, cells are incubated with medium containing AGE-TF treated, insoluble or aggregated labelled βAP or amylin versus control (e.g., labelled flAP or amylin alone, TF alone and/or TF treated labelled βAP or amylin) for various times, ranging from 1–48 hours, e.g., 1, 2, 4, 24 and 48 hours, at 37° C. After the incubation, the cells are separated from the culture fluid. The content of label in the cell fraction and culture fluid fraction is measured, e.g., by TCA precipitation of the labelled compounds. Alternatively, wells can be pre-coated with the labelled test and control compounds, in either their soluble or insoluble aggregated forms, incubated with cells, and the presence of labelled compounds in the cell culture fluid, which is indicative of degradation of the compounds by uptake of the compounds coated on the wells, can be assayed. Preferably, the label is 125I or FITC, more preferably 125I. The uptake assay can be performed with the same cells as used for the clearance assay.

The invention also contemplates use of in vivo assays to demonstrate AGE modification of amyloid. In one embodiment, AGE-TF or AGE-Congo Red can be administered to female Syrian hamsters, which develop amyloidosis in the liver, spleen and kidney within about one year after birth (resulting in a much shorter life expectancy than for male hamsters; see Coe and Ross, 1985, J. Clin. Invest. 76:66–74), and in which administration of diethylstilbestrol (DES) accelerates this amyloidosis. To determine the effect of AGE-TF or AGE-Congo Red, a group (n=4 to 10) of 6–12 month old hamsters treated with DES at 3 months of age are treated with 1–2 intraperitoneal injections of about 0.1 to about 1 mg of AGE-TF or AGE-Congo Red in an appropriate carrier, such as buffered saline, per week for varying periods of time. Control animals receive injections of the carrier, AGE alone, and TF or Congo Red alone. The presence and level of AGE-modification of amyloid deposits can be tested by the tissue squash method (Coe and Ross, 1990, J. Exp. Med. 171:1257–67) and ELISA (as described herein) after varying periods of time, e.g., 1 month, 2 months, and 4 months.

A similar in vivo assay can be performed on mice or hamsters inoculated intraperitoneally or intracranially with scrapie. About 1 month to 12 months, preferably 1 month to about 6 months, after infection with scrapie, the animals can be treated with AGE-TF or AGE-Congo Red, e.g., weekly or biweekly with intraperitoneal or intracranial injections of about 0.1 to about 1 mg of AGE-TF or AGE-Congo Red. Tissue samples or sections of affected organs (spleen for intraperitoneal infection, brain for intracranial infection) can be obtained. The presence of amyloid in spleen or brain can be detected histologically or immunochemically (immunohistologically or by ELISA with an anti-PrP antibody). The level of AGE modification of the tissue can be detected immunohistologically or by ELISA, e.g., using the anti-AGE-RNase antibody as described herein.

Such an experiment can also be performed with cats, rats, or mice that are genetically predisposed or treated to develop a Type II diabetic condition. About 1 month to 12 months, preferably 1 month to about 6 months, after diabetes onset, the animals can be treated with AGE-TF or AGE-Congo Red, e.g., weekly or biweekly with intraperitoneal or intravenous injections of about 0.1 to about 1 mg of AGE-TF or AGE-Congo Red. Tissue samples or sections of pancreas, particularly areas containing islet cells, can be obtained. The presence of amyloid can be detected histologically or immunochemically (immunohistologically or by ELISA). The level of AGE modification of the tissue can be detected immunohistologically or by ELISA, e.g., using the anti-AGE-RNase antibody as described herein.

The effectiveness of AGE modification of amyloid in inducing removal of the amyloid can be determined by detecting the amount of amyloid in affected tissues and comparing that amount to the amount in control animals after various periods of time. According to this aspect of the invention, the time course of pathology and treatment can involve amyloidosis, AGE-modification of amyloid, and clearance of the AGE-modified amyloid. Thus, the presence of amyloid and the level of AGE modification of the amyloid will depend on the point within the time course at which the sample is obtained for testing. The time course can be readily determined by obtaining and assaying samples at various times.

In a further embodiment, the method of inducing AGE modification of the amyloid can be combined with the methods discussed above for activating mechanisms for the recognition and clearance of AGE-modified amyloid plaques.

Diagnostic Methods

The present invention also relates to a method for detecting the presence of or monitoring the course of a disease or disorder associated with amyloidosis comprising detecting the presence of or measuring the level or amount of an AGE-amyloid polypeptide that is found in the amyloid plaques characteristic of such a disease. Detecting the presence of AGE-amyloid polypeptides can indicate the existence of the disease condition, and thus may be useful alone or in conjunction with other criteria in diagnosis of such a disease. An increase in the level of AGE-amyloid polypeptide compared to the level detected in the subject at an earlier time, or to the level found in normal individuals, can indicate disease progression; a decrease in the level compared to the level in the subject at an earlier time, or the level found in normal individuals, can indicate regression of the disease.

In a specific aspect, the invention provides for diagnosing or monitoring the course of a neurodegenerative disease associated with amyloidosis in mammals, by measuring the corresponding presence and amount or level of AGE-βAP. AGE-βAP can be detected in biological fluids such as, but not limited to, blood, plasma, serum, urine, cerebrospinal fluid, and the like. Alternatively, the sample can be a histopathological sample, such as a biopsy or tissue sample.

In another embodiment, the invention relates to a method for detecting the presence of or monitoring the course of Type II diabetes by measuring the corresponding presence or amount or level of AGE-amylin. AGE-amylin can be detected in biological fluids, such as, but not limited to, blood, plasma, serum, urine, peritoneal fluid, and the like. Alternatively, the sample can be a histopathological sample, such as a biopsy or tissue sample.

The presence or level of AGEs may be followed directly by assay techniques such as those discussed herein, through the use of an appropriately labeled quantity of at least one of the binding partners to AGE-amyloid polypeptide as set forth herein. Alternately, AGEs can be used to raise binding partners or antagonists that could in turn, be labeled and introduced into a medium to test for the presence and amount of AGEs therein, and to thereby assess the state of the host from which the medium was drawn.

The term "ligands" includes such materials that would bind to AGE-amyloid peptide-binding partners, and would include such materials as are prepared by the reaction of AGE-flAP or AGE-amylin with avidin or biotin, or the preparation of synthetic AGE-flAP or AGE-amylin derivatives that may be prepared from the reaction of βAP or amylin with reducing sugars such as glucose, glucose-6-phosphate (G-6-P), fructose or ribose, and AGE-fAP or AGE-amylin conjugation with peptides, proteins and other biochemicals such as bovine serum albumin (BSA), avidin, biotin derivatives, and enzymes such as alkaline phosphatase. Likewise, enzymes and other carriers that have undergone advanced glycosylation may also serve as ligands in any of the assays of the present invention. Accordingly, carriers such as carbohydrates, proteins, synthetic polypeptides, lipids and biocompatible natural and synthetic resins, and any mixtures of the same may be reacted with sugars to form advanced glycosylation endproducts and may thereby be useful in the present methods. The present diagnostic methods are intended to contemplate all of the foregoing materials within their scope.

The term "AGE binding partners" is intended to extend to anti-AGE antibodies and to other cellular AGE binding proteins or receptors for AGEs, which AGEs may be found on peptides, molecules and cells. A particular AGE binding partner is an anti-AGE antibody raised in rabbits and isolated therefrom for use as contemplated herein.

Thus, both AGE-βAP or AGE-amylin and any binding partners thereto that may be prepared, are capable of use in connection with various diagnostic techniques, including immunoassays, such as a radioimmunoassay, using for example, a receptor or other ligand to an AGE that may either be unlabeled or if labeled, e.g., by radioactive addition or radioiodination.

In an immunoassay, a control quantity of a binding partner to AGE-βAP or AGE-amylin may be prepared and optionally labeled, such as with an enzyme, a compound that fluoresces and/or a radioactive element, and may then be introduced into a tissue or fluid sample of a mammal. After the labeled material or its binding partner(s) has had an opportunity to react with sites within the sample, the resulting mass may be examined by known techniques, which may vary with the nature of the label attached.

The labels most commonly employed for these studies are radioactive elements, enzymes, chemicals which fluoresce when exposed to ultraviolet light, and others.

Suitable examples of radioactive elements include $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{113}$I, and $^{186}$Re. In the instance where a radioactive label, such is prepared with one of the above isotopes is used, known currently available counting procedures may be utilized.

In the instance where the label is an enzyme, detection may be accomplished by any of the presently utilized colorimetric, spectrophotometric, fluorospectrophotometric, thermometric, amperometric or gasometric techniques known in the art. The enzyme may be conjugated to the advanced glycosylation endproducts, their binding partners or carrier molecules by reaction with bridging molecules such as carbodiimides, diisocyanates, glutaraldehyde and the like.

Many enzymes which can be used in these procedures are known and can be utilized. The preferred are peroxidase, 6-glucuronidase, β-D-glucosidase, β-D-galactosidase, urease, glucose oxidase plus peroxidase, hexokinase plus GPDase, RNAse, glucose oxidase plus alkaline phosphatase, NAD oxidoreductase plus luciferase, phosphofructokinase plus phosphoenol pyruvate carboxylase, aspartate aminotransferase plus phosphoenol pyruvate decarboxylase, and alkaline phosphatase. U.S. Pat. Nos. 3,654,090; 3,850,752; and 4,016,043 are referred to by way of example for their disclosure of alternative labeling material and methods. A particular enzymatic detecting material is anti-rabbit antibody prepared in goats and conjugated with alkaline phosphatase through an isothiocyanate.

A number of fluorescent materials are known and can be utilized as labels. These include, for example, fluorescein, rhodamine and auramine. A particular fluorescent detecting material is anti-rabbit antibody prepared in goats and conjugated with fluorescein through an isothiocyanate.

In addition to therapeutic uses, the antibodies of the invention can be used to detect AGE-amyloid polypeptides in amyloid or in solution. In particular, antibodies of the invention can be used to determine the amount and location of the AGE in amyloid plaques in the mammalian body. For convenience, the antibody(ies) to the AGE will be referred to herein as Ab, and antibody(ies) reactive with $Ab_1$ as $Ab_2$.

The amount of AGE-amyloid polypeptide in a biological fluid or the degree of advanced glycosylation in amyloid plaques can be ascertained by the usual immunological procedures applicable to such determinations. A number of useful procedures are known. Three such procedures which are especially useful utilize either the AGE-amyloid polypeptide labeled with a detectable label, antibody Ab, labeled with a detectable label, or antibody $Ab_2$ labeled with a detectable label. The procedures and their application are all familiar to those skilled in the art and accordingly may be utilized within the scope of the present invention. An example of a "competitive" procedure is described in U.S. Pat. Nos. 3,654,090 and 3,850,752. An example of a "sandwich" procedure, is described in U.S. Pat. Nos. RE 31,006 and 4,016,043. Still other procedures are known such as the "double antibody", or "DASP" procedure.

In each instance, the AGE-modified substance forms complexes with one or more antibody(ies) or binding partners and one member of the complex is labeled with a detectable label. The fact that a complex has formed, and, if desired, the amount thereof, can be determined by known methods applicable to the detection of labels.

It will be seen from the above, that a characteristic property of Ab2 is that it will react with $Ab_1$. This is because an antibody raised in the mammalian species in which $Ab_1$ was raised has been used in another species as an antigen to raise the antibody $Ab_2$. For example, $Ab_1$ may be raised in rabbits and $Ab_2$ may be raised in goats using a rabbit Ab as an antigen. $Ab_2$ therefore would be anti-rabbit antibody raised in goats.

Accordingly, a test kit may be prepared for the demonstration of AGE-amyloid polypeptide in a sample, comprising:

(a) a predetermined amount of at least one labeled immunochemically reactive component obtained by the direct or indirect attachment of AGE-amyloid polypeptide or an AGE binding partner to a detectable label;

(b) other reagents; and (c) directions for use of said kit.

More specifically, the diagnostic test kit may comprise:

(a) a known amount of an AGE, such as AGE-BSA, AGE-βAP, or AGE-amylin (or a binding partner thereof) generally bound to a solid phase to form a immunosorbent, or in the alternative, bound to a suitable tag, or plural such components, etc. (or their binding partners) one of each;

(b) if necessary, other reagents; and (c) directions for use of said test kit.

By example, a solid phase assay system or kit may comprise the solid substrate with either bound binding partner and labeled AGE-amyloid polypeptide or bound AGE-amyloid polypeptide and labeled binding partner. A sample to be assayed is then placed in contact with the bound and unbound reagent. A competitive reaction between the labeled material and any unlabeled binding partner(s) in the sample will cause the retention of a dependent quantity of the former on the solid substrate, whereupon it can be precisely quantitatively identified. The foregoing explanation of a particular competitive assay system is presented herein for purposes of illustration only, in fulfillment of the duty to present an enabling disclosure of the invention. It is to be understood that the present invention contemplates a variety of diagnostic protocols within its spirit and scope.

In a preferred aspect of the invention, the AGE assay described in Makita et al. (1992, J. Biol. Chem. 267:5133–38) is used to detect the presence and determine the amount of AGE-amyloid in a tissue sample, particularly a sample that contains amyloid, or the amount of AGE-βAP, AGE-scrapie protein, or AGE-amylin present in a sample.

In a specific embodiment, infra, antibodies reactive with AGEs are used to detect increased levels of AGE-proteins in brain tissue from individuals diagnosed with AD compared to normal individuals.

In another specific embodiment, antibodies to PrP (the scrapie or prion protein; e.g., Kascsak et al., 1987, J. Virol. 61:3688–3693) and antibodies to AGE can be used to show co-localization of these epitopes in a tissue sample. For example, brain sections from hamsters or mice infected with scrapie can be immunohistochemically stained with rabbit polyclonal anti-PrP, anti-AGE-RNase, and a control anti-RNase. In scrapie (a subacute spongiform encephalopathy), the characteristic spongiform encephalopathy is characterized by PrP-associated lesions, which contain amyloid deposits. These immunochemical studies can show that within a single scrapie diseased brain, PrP and AGEs co-localize in the amyloid of these lesions.

The invention may be more completely understood by reference to the following non-limiting examples, which are provided solely as exemplary of specific embodiments of the invention.

EXAMPLE 1

Age-Amyloid in Alzheimer's Disease

Alzheimer's disease (AD) is characterized by deposits of aggregated β-amyloid peptide (βAP) in the brain and cerebrovasculature. After a concentration-dependent lag period during in vitro incubations, soluble preparations of synthetic βAP slowly form fibrillar aggregates that resemble natural amyloid and are measurable by sedimentation or Thioflavin-T-based fluorescence. Aggregation of soluble βAP in these in vitro assays is enhanced by addition of small amounts of pre-aggregated β-amyloid "seed" material. These seeds have also been prepared herein using a naturally occurring reaction between glucose and protein amino groups resulting in the formation of advanced glycosylation endproducts (AGEs) which chemically crosslink proteins. AGE-modified βAP-nucleation seeds further accelerated aggregation of soluble βAP compared to non-modified "seed" material. Over time, nonenzymatic advanced glycosylation also results in the gradual accumulation of a set of post-translational covalent adducts on long-lived proteins in vivo. Using a standardized competitive ELISA assay, plaque fractions of AD brains were found to contain about 3-fold more AGE adducts per mg protein than found in like preparations from healthy, age-matched controls. These results indicate that the in vivo half-life of B-amyloid is prolonged in AD, resulting in greater accumulation of AGE modifications, which in turn can act to promote accumulation of additional amyloid.

Materials and Methods

Aggregation and Seeding Reactions.

Synthetic, HPLC-purified peptides representing the first 28 (βAP 1–28) and the first 40 amino acids (βAP 1–40) of the 42 amino acid βAP were obtained from Bachem (Torrance, Calif.). Aggregation of soluble βAP 1–28 or 3AP 1–40 at different concentrations was initiated by addition of 0.1 M sodium acetate (NaOAc) at the indicated pH (between 4.7 and 7.5) and continued for the indicated times. Quantitative aggregate formation with sub-millimolar βAP concentrations was detected using the procedure of LeVine (1992, Protein Science 2:404–410). Briefly, fluorescence of aggregates added to 10 $\mu$M Thioflavin-T (Aldrich)/50 mM potassium phosphate buffer, pH 6.0, was measured upon excitation at 450±5 nm and detection of emission at 482±10 nm on a Perkin Elmer LS-50B spectrofluorimeter. Where indicated, small amounts of pre-formed aggregates or "nucleation seeds" were added to the soluble βAP and aggregation initiated with 0.1 M sodium acetate.

Generations of "Seeds".

Soluble βAP 1–40 (250 $\mu$M) and 0.2 M sodium phosphate buffer, pH 7.5, were incubated with or without 1 M glucose at 37° C. to generate pre-formed aggregates of AGE-βAP referred to as "AGE-βAP seed" or "βAP seed", respectively. After incubation, protein concentrations of seed preparations were measured and adjusted with buffer to 150 $\mu$M final concentration. Using competitive ELISA (Makita et al., supra), AGE-βAP seed contained 50 AGE Units/mg protein and βAP seed contained less than 0.5 AGE Units/mg protein. Lysines at positions 16 and 28 of βAP contain primary amino groups which may react with reducing sugars to generate advanced glycosylation endproducts of AGEs. Indicated amounts of glucose and/or aminoguanidine, a potent inhibitor of advanced glycation and crosslink formation (Brownlee et al., 1986, Science 232:1629–1632), were also added to solutions of βAP before sodium acetate in some experiments.

Aggregation of βAP at lower (physiological) concentrations was quantitated by the method of Burdick et al. (1992, J. Biol. Chem. 267:546–554). Synthetic preparations of βAP 1–40 were labeled with 1251 (NEN) and chloramine-T (Sigma) for 1 minute before the reaction was quenched with 10 mM tyrosine and sodium meta-bisulfite. Unincorporated label was removed by filtration through a SEPHADEX G-10 column equilibrated in 0.5×phosphate buffered saline (PBS), pH 7.4. The $^{125}$I-labeled βAP (approximate specific activity of $3\times10^6$ cpm/$\mu$g) was immediately diluted to 5 riM final concentration in the presence of various "seeds," glucose and/or aminoguanidine at the indicated concentrations. After various incubation periods at 37° C., aggregation reactions were underlayed with 20% sucrose/0.1 M sodium acetate at the same pH as the incubation mixture, centrifuged for 30 minutes at 50,000×g, and frozen in liquid nitrogen. Each microfuge tube was cut and the bottom 5 mm representing the aggregated sedimentable fraction which had pelleted through the sucrose cushion, was counted in a gamma counter. The remainder of the tube and liquid were also counted. The amount of aggregate formed was calculated as a percentage equal to the number of counts in the pellet divided by the total number of counts per tube (pellet +remainder) multiplied by 100.

Measurement of AGEs with Competitive ELISA.

Aliquots of frozen pre-frontal cortex (Brodman areas 9 and 10) from patients with and without behaviorally and neuropathologically confirmed AD were resuspended in 10 volumes per wet weight of 2% sodium dodecylsulfate (SDS)/0.1 M B-mercaptoethanol (ME), and Dounce homogenized. The homogenate was boiled for 10 minutes and then centrifuged at 10,000×g for 10 minutes. Supernatants were aspirated and the resulting pellets washed three times with PBS at 10,000×g for 10 minutes. In some experiments, this crude plaque fraction was further washed twice with 4 M urea and twice more with PBS before protease digestion. PBS-washed pellets were resuspended in one-tenth the original homogenate volume of PBS and 0.1% Proteinase-K (Boehringer Mannheim), digested overnight at 37° C. and heat inactivated at 75° C. for 3 hours. Quadruplicate 5, 10 and 20 $\mu$l aliquots of plaque-containing pellet fractions were assayed for AGE content using a competitive ELISA (Makita et al., 1992, J. Biol. Chem. 267:5133-38), against standardized preparation of AGE-modified bovine serum albumin (AGE-BSA). Only values in the linear range of the standard curve were included in the analyses.

Protein amounts were quantitated with micro-BCA kit (Pierce) and with fluorescamine (Bohlen et al., 1973, Arch. Biochem. Biophys. 155:213–220). AGE Units were interpolated from a standard dilution curve of AGE-BSA and divided by the sample protein concentration to give AGE Units per mg protein. Statistical analysis using Student's test was performed with the StatWorks program for Macintosh using a Macintosh personal computer (Apple Computer, Inc.).

Results

βAP Aggregation. Displays Nucleation Dependent Kinetics.

Aggregation of synthetic βAP was analyzed in vitro where the aggregation rate of soluble βAP was found to depend mainly upon pH and the initial concentration. The kinetics of aggregation were determined empirically. 600 $\mu$M βAP 1–28 spontaneously and rapidly formed Thioflavin-T fluorescent aggregates within minutes at pH 7.2 (FIG. 1). At concentrations below 300 AM, however, βAP aggregated very slowly with a considerable lag before fluorescent aggregates were measurable.

Figure 2:
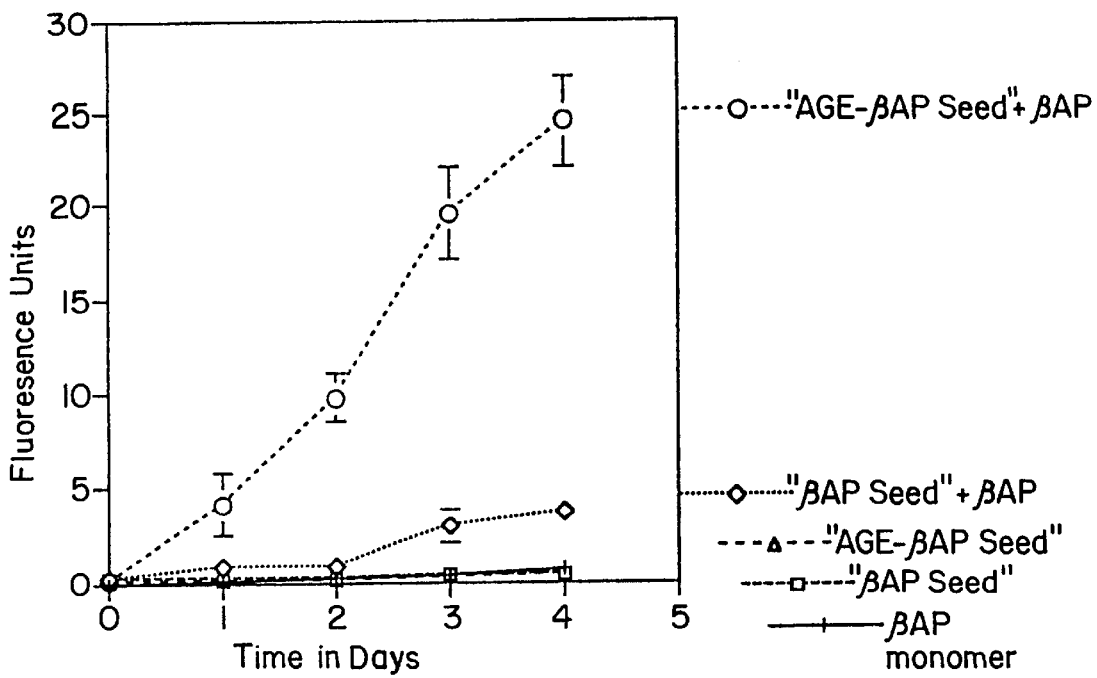
FIG. 2 presents a graph demonstrating that fluorescent aggregate formation displays nucleation-dependent kinetics. Stable aggregates of synthetic βAP were formed in the presence or absence of glucose to generate "AGE-βAP seed" and "βAP seed." Seeds were added to 300 $\mu$M soluble βAP and incubated for different times. The mean ±standard error of triplicate Thioflavin-T fluorescence measurements is plotted as a function of time for "AGE-βAP seed"+βAP (circles) and "βAP seed"+βAP (diamonds). Control incubations included "AGE-βAP seed" alone (triangles), "βAP seed" alone (squares) and soluble βAP without seeding (crosses).

At low concentrations of βAP, the lag period preceding measurable aggregation is reminiscent of crystallization reactions, in which protein solutions very slowly assume a single conformation and aggregate in a well-defined, molecular packing arrangement (Jarrett et al., 1993, Biochemistry 32:4693–4697; Jarrett and Lansbury, 1993, Cell 73:1055-1058; Come et al., 1993, Proc. Natl. Acad. Sci. USA 90:5959–5963). The kinetics of such aggregation in many cases can be significantly accelerated by the addition of a pre-formed aggregate or "seed" material as nucleation centers for additional aggregate formation. Stable "βAP seed" material was prepared by incubating 250 AM βAP 1–40 for 4 months at 37° C. Compared to the small amounts of fluorescent aggregate measured when 300 μM soluble βAP or 75 μM "βAP seed" were separately incubated in control preparations, co-incubation of soluble βAP plus "βAP seed" resulted in the progressive accumulation of much larger amounts of fluorescent aggregates (FIG. 2).

AGE-modified βAP seed was also prepared by incubating soluble βAP in 1 M glucose/pH 7.5 phosphate buffer at 37° C. for 4 months ("AGE-βAP seed"). AGE formation was confirmed by competitive ELISA where "βAP seed" contained less than 0.5 AGE Units/mg protein and "AGE-βAP seed" contained 50 AGE Units/mg protein, which is comparable, within an order of magnitude, to the AGE content of plaques from AD brains (see below). When 75 μM "AGE-βAP seed" was co-incubated with 300 μM soluble βAP, much more fluorescent aggregate was detected than in parallel incubations with unmodified "βAP seed" and soluble βAP (FIG. 2). As with "βAP seed," separate incubation of "AGE-βAP seed" alone did not lead to a change in the small amount of fluorescent aggregate with time.

Figure 3:
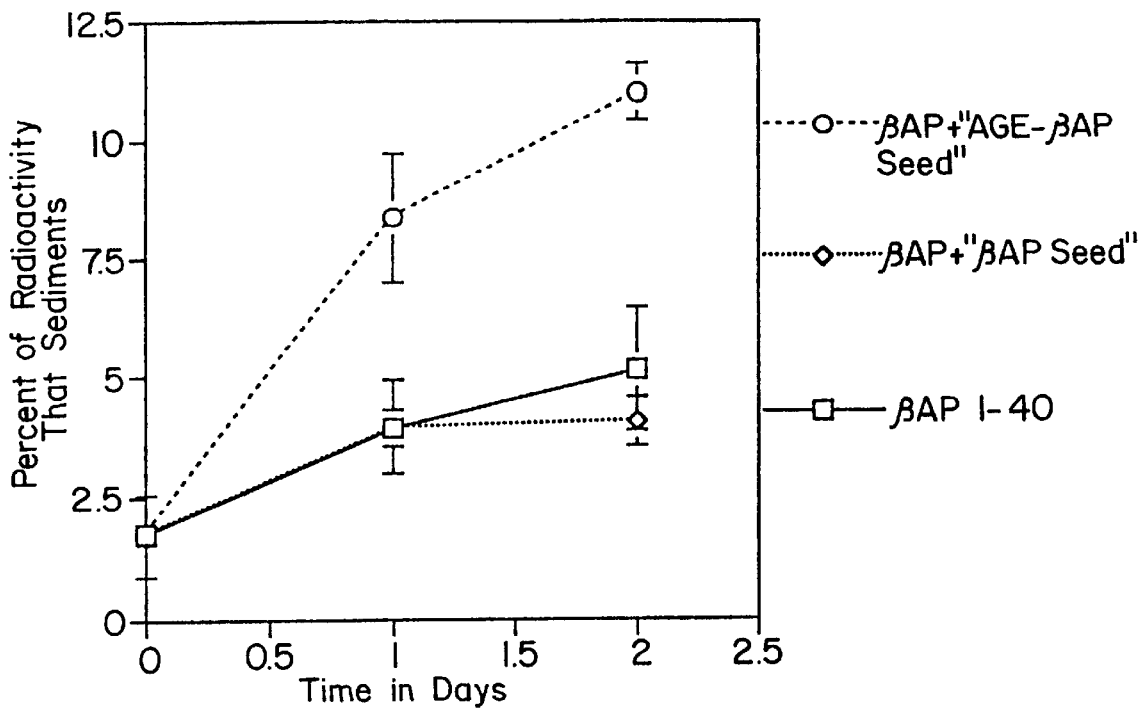
FIG. 3 demonstrates that "AGE-βAP seeds" nucleate more aggregation at physiological concentrations of βAP than "βAP seeds." 10 nM $^{125}$I-βAP 1–40 was mixed with no seed (squares), "βAP seed" (diamonds) or "AGE-βAP seed" (circles) and incubated for the indicated times at 37° C. The mean ±standard error of quadruplicate measurements is plotted.

To test whether this seeding phenomenon occurs at concentrations of βAP that are typically found in vivo, a sedimentation assay was employed to measure aggregation. Aggregation of 10 nM solutions of soluble $^{125}$I-labelled synthetic βAP 1–40 in 0.1 M sodium acetate, pH 7.0, increases slowly over a two-day incubation (FIG. 3). If 10 nM labeled RAP was co-incubated with 200 nM unlabeled "βAP seed" material, the amount of sedimentable label was similar to the no seed, soluble βAP only curve. In contrast, co-incubation of 10 nM soluble βAP with 200 nM "AGE-βAP seed" increased the amounts of sedimentable label compared to the "βAP seed" and no seed experimental points. Thus, the amount of labeled βAP associated with sedimentable aggregates observed in co-incubations of soluble βAP and "AGE-βAP seed" is greater than that formed in co-incubations with "OAP seeds" or no seed under conditions in which pH and soluble βAP concentrations are physiological.

Glucose Modifies Kinetics of Aggregation.

Figure 4:
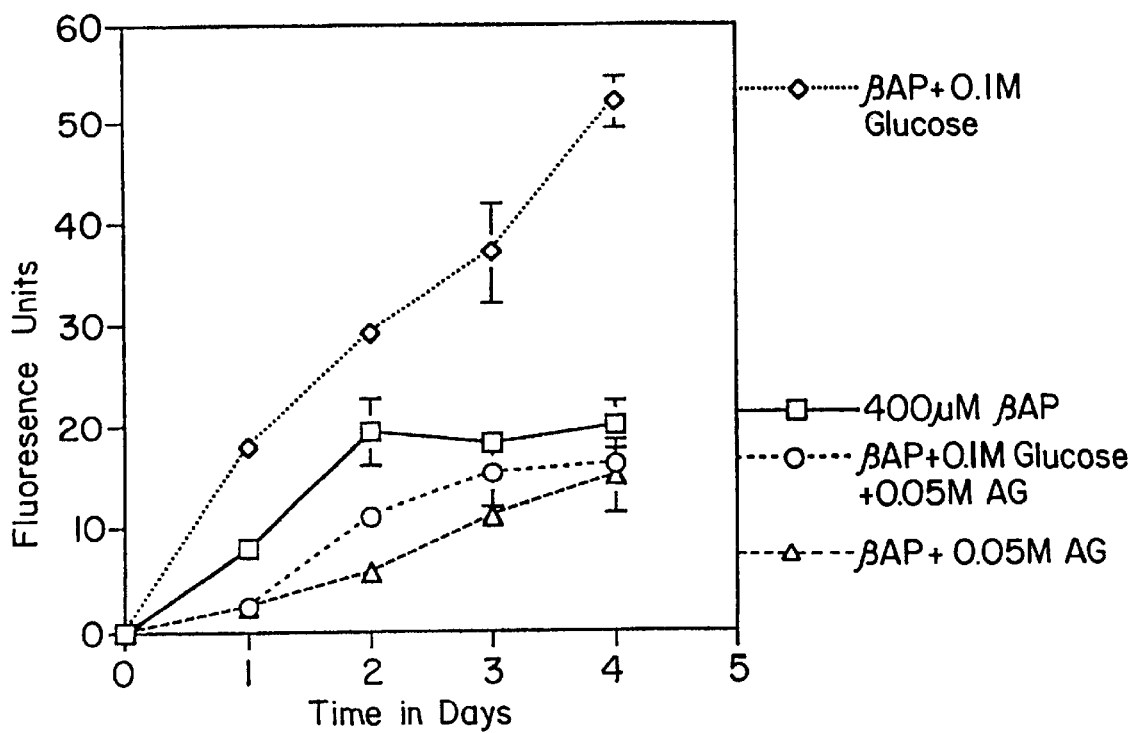
FIG. 4 is a graph showing that glucose modifies the kinetics of fluorescent aggregate formation. Soluble βAP (400 $\mu$M βAP 1–28), 0.1 M sodium acetate in 0.1 M phosphate buffer, pH 7.0 (squares), were mixed with 0.1 M glucose (diamonds), 0.05 M aminoguanidine (AG, triangles), or glucose and aminoguanidine (circles). The mean ±standard error of triplicate Thioflavin-T fluorescence measurements is plotted on this graph.

In the process of advanced glycosylation, formation of a Schiff base between glucose and a protein amino group precedes subsequent maturation of Amadori products into AGE-modified βAP. Aminoguanidine is a compound which prevents AGE formation following initial glucose reactions with protein amines (Brownlee et al., 1986, Science 232:1629-1632). Co-incubation of 400 tM βAP 1–28 in 0.1 M sodium acetate, pH 7.0, with 100 mM glucose stimulates fluorescent aggregate formation when compared to parallel incubations of soluble βAP, soluble βAP+AG, or soluble βAP+AG+glucose (FIG. 4). Separate incubations of glucose or AG failed to generate detectable fluorescent signals.

AGE Content of Brain Fractions.

On average, plaque-enriched fractions isolated from samples of pre-frontal cortex of 10 AD brains contained significantly more AGE modifications than did corresponding preparations from 7 healthy controls (8.9±1.4 versus 2.7±0.5 AGE Units/mg protein, p=0.002, see FIG. 5). The average chronological age of both the AD and control groups was 77 years. The presence of AGEs in similar fractions of parietal cortex from AD and normal brains has also been observed (data not shown). Supernatant fractions of SDS-soluble proteins from AD and control brains routinely contained less than 0.1 AGE Units/mg protein.

Discussion

Although advanced glycosylation adducts form spontaneously in vivo, their accumulation is slow and becomes most notable with increasing time on long-lived tissue components. Along with time and the availability of susceptible protein amino groups, ambient glucose is the other major determinant of AGE formation. Thus, quantitative analysis of the degree of AGE modification of a single protein species under standardized glycemic conditions yields an index of the protein's half-life in vivo. It was found that plaque-enriched fractions isolated from AD brain samples contained about 3-fold more AGE modifications than did comparable fractions prepared from age-matched control brains, suggesting that RAP half-life is prolonged in AD. That amyloid components exhibit a prolonged half-life in AD is also supported by studies that demonstrated the time-dependent, nonenzymatic isomerization of aspartyl-residues occurring at positions 1 and 7 of βAP isolated from AD brain (Roher et al., 1993, J. Biol. Chem. 268:3072–3083), although this study latter did not include normal controls.

AD is characterized by progressive dementia and increased numbers and amount of amyloid plaques compared to healthy age-matched controls. While a causal relationship between increased dementia and plaque numbers has not been proven, the gradual onset of symptoms appears to parallel the progressive deposition of β-amyloid. From in vitro studies, it is clear that millimolar concentrations of soluble βAP will spontaneously aggregate into fibrillar amyloid structures following a nucleation-dependent mechanism. At lower concentrations, the requirement for nucleus formation introduces a substantial lag period during which a solution of βAP that still requires most of this time to form aggregation nuclei is indistinguishable from one on the verge of rapid aggregation and growth into a "one dimensional crystal" (Jarrett and Lansbury, 1993, Cell 73:1055–1058). The effect of this concentration-dependent nucleus formation is extreme as illustrated by published calculations that show an APP mutation in a Swedish form of familial AD which raises soluble βAP concentrations 6-fold (Cai et al., 1992, Science 259:514–516; Citron et al., 1992, Nature 360:672–674) should reduce the lag time before aggregate growth occurs from 100 years to about 3 hours (Jarrett et al., 1993, Biochem. 32:4693–4697). Since the cerebrospinal fluid concentration of soluble βAP in AD patients is the same as in age-matched controls (Oosawa et al., 1993, Soc. Neurosci. Abs. 19:1038; Shoji et al., 1992, Science 258:126, 129), the rate of concentration-dependent self-formation of nuclei, as reflected by the amounts of amyloid formed and deposited, might also be expected to be the same. As this latter similarity is not observed and AD brains form substantially more deposits of aggregated βAP than their non-diseased counterparts, then it appears that the increased amount of amyloid present in afflicted brain tissue results, at least in part, from more efficient nucleated aggregation than occurs in healthy brain parenchyma.

For purposes of clarifying the operation and discovery of the invention, but without intending to be limited to any particular theory or hypothesis by way of this explanation, nucleation seeds can be thought of as structures of βAP possessing a specific conformation that promotes the rapid accretion of additional soluble βAP resulting in the growth of insoluble βAP aggregates. Since the spontaneous formation of nuclei is thermodynamically unfavorable (Jarrett et al., 1993, supra), processes known to chemically crosslink proteins in vivo might serve to stabilize specific conformations of βAP with nucleating characteristics. Advanced glycosylation is a naturally occurring process of covalent post-translational modification of proteins that readily occurs extracellularly. AGEs in other contexts are well-known as protein-protein crosslinking agents in vivo and in vitro, and AGE accumulation on matrix proteins is associated with increased resistance to proteolysis (Bucala et al., 1992, in *Post-Translational Modifications of Proteins*, Harding et al., Eds., CRC Press, Boca Raton 2:53–79).

At physiological concentration and pH in vitro, soluble βAP aggregates slowly. Of note, the addition of preformed aggregates of AGE-modified-βAP stimulated markedly more rapid aggregation of nM solutions of soluble βAP than did preformed aggregates of unmodified βAP in two-day incubations. That this acceleration occurred at normal pH, physiological concentrations of soluble βAP, and with seeds containing amounts of AGE-modifications comparable to those found in AD plaque fractions, suggests that a similar process could occur in vivo.

Glycation adducts comprise a structurally heterogeneous family of products that slowly evolve chemically by a variety of rearrangement, condensation and elimination reactions. The particular AGE species that enhance nucleation remain unknown, but these may be relatively early glycosylation products, as evidenced by the time course over which glucose accelerated the rate of fluorescent βAP aggregate formation compared to aggregation in the presence of glucose and aminoguanidine, a specific inhibitor of AGE formation. Recognizing that plaque numbers increase in association with neuronal degeneration and cognitive decline in AD, and that aggregated but not soluble βAP is actively neurotoxic (Pike et al., 1991, Eur. J. Pharm. 207:367–368; Pike et al., 1993, J. Neuroscience 13:1676–1687), interference with the processes by which AGE formation enhances βAP aggregation can provide new therapeutic opportunities to reduce the pathophysiological changes associated with AD.

EXAMPLE 2

Co-Localization of Ages and Prion Protein H amsters were infected by intracerebral injection with a strain of hamster-adapted murine scrapie. After 300 days, the hamsters were sacrificed, the brains sectioned, and the sections fixed on microscope slides. The fixed sections were treated with 70%. formic acid for 10 minutes and washed. The slides were then reacted with rabbit antisera specific for RNase (control antisera), prion protein (PrP; Kascsak et al., 1987, J. Virol. 61:3688–93), and AGE (anti-AGE-RNase antisera, as described in Makita et al., 1992, J. Biol. Chem. 267:5133–38). Each serum was diluted 1:500 prior to incubation with the tissue samples. The reactions were incubated overnight at 4° C. Following reaction with the rabbit antisera, the samples were washed with PBS and reacted with an alkaline phosphatase (AP)-conjugated anti-rabbit antibody. The samples were developed with a fuschin AP substrate (Dako), which produces a red color.

Figure 6A:
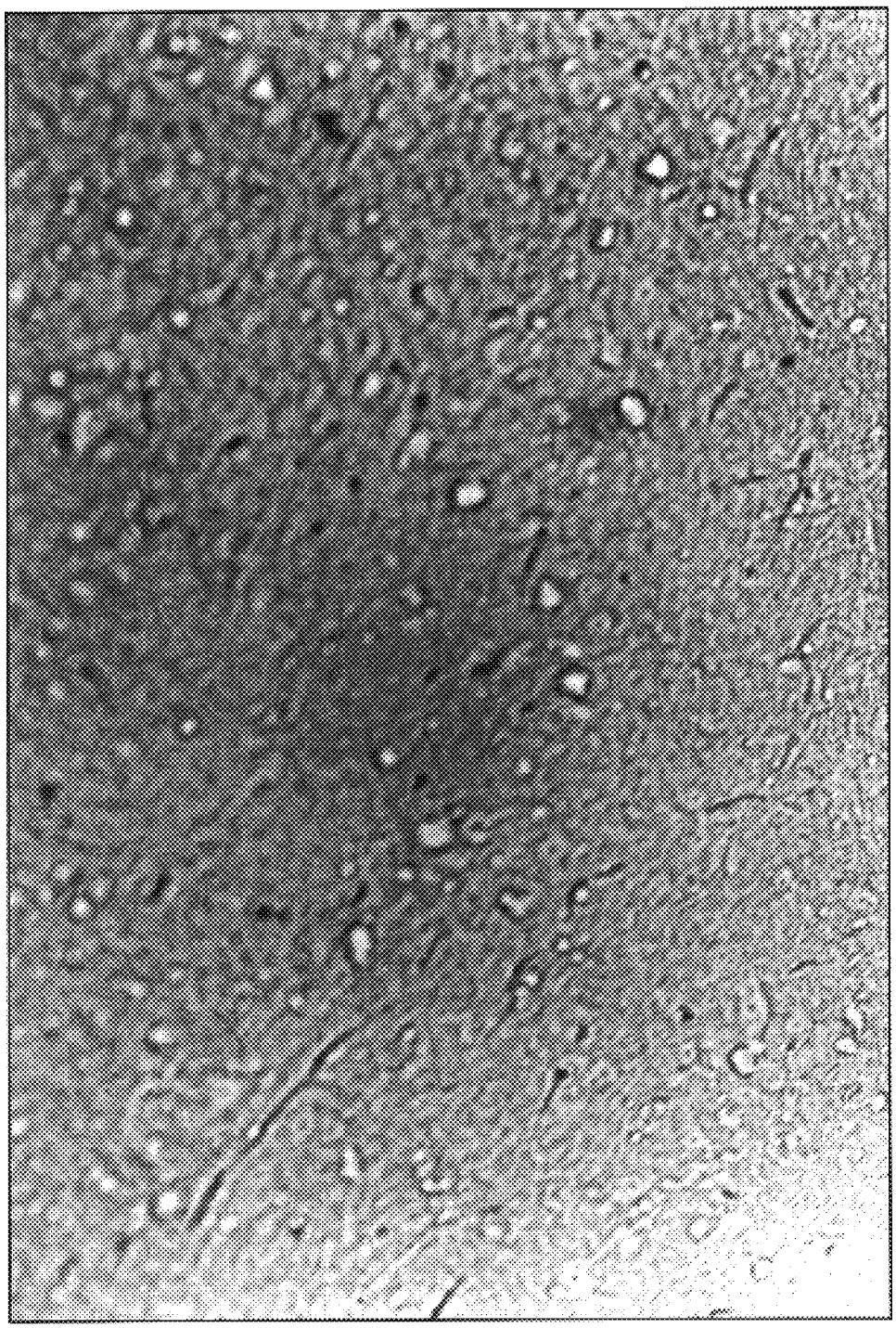
FIG. 6 presents photographs that demonstrate the co-localization of AGE and prion protein (PrP) in PrP associated lesions, which contain amyloid deposits, characteristic of the spongiform encephalopathy found in the neurodegenerative disease scrapie. Brain tissue sections were obtained from 300 day old hamsters intracranially infected with a strain of hamster scrapie, reacted with control or specific polyclonal rabbit antisera, followed by a second alkaline phosphatase-conjugated anti-rabbit antibody to detect rabbit antibodies. (A) Rabbit anti-RNase at 1:500 dilution (control); (B) Rabbit anti-PrP at 1:500 dilution; (C) rabbit anti-AGE-RNase (Makita et al., 1992, J. Biol. Chem. 267:5133–38) at a 1:500 dilution. Note that similar structures are decorated by the rabbit antisera in (B) and (C).
Figure 6B:
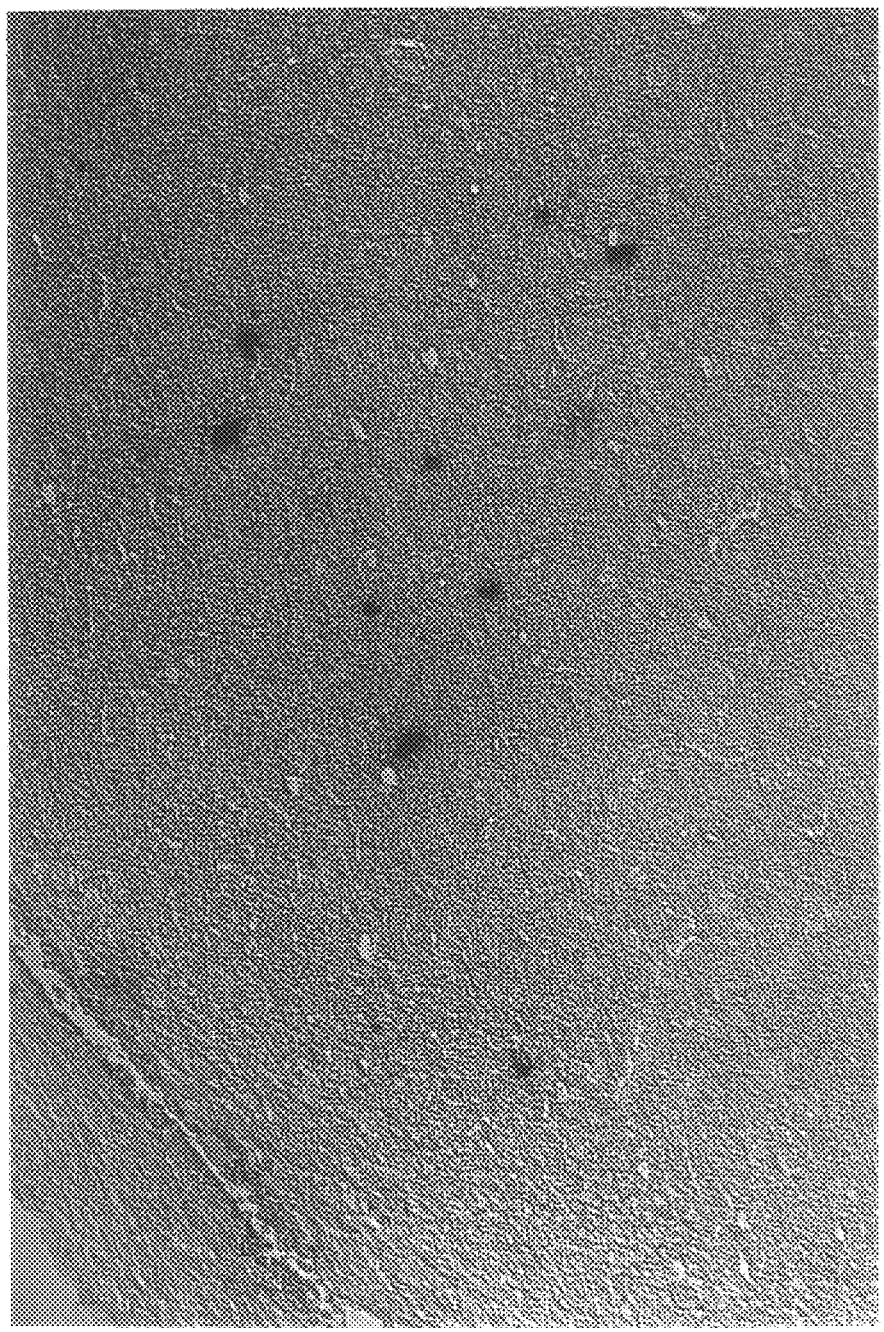
Figure 6C:
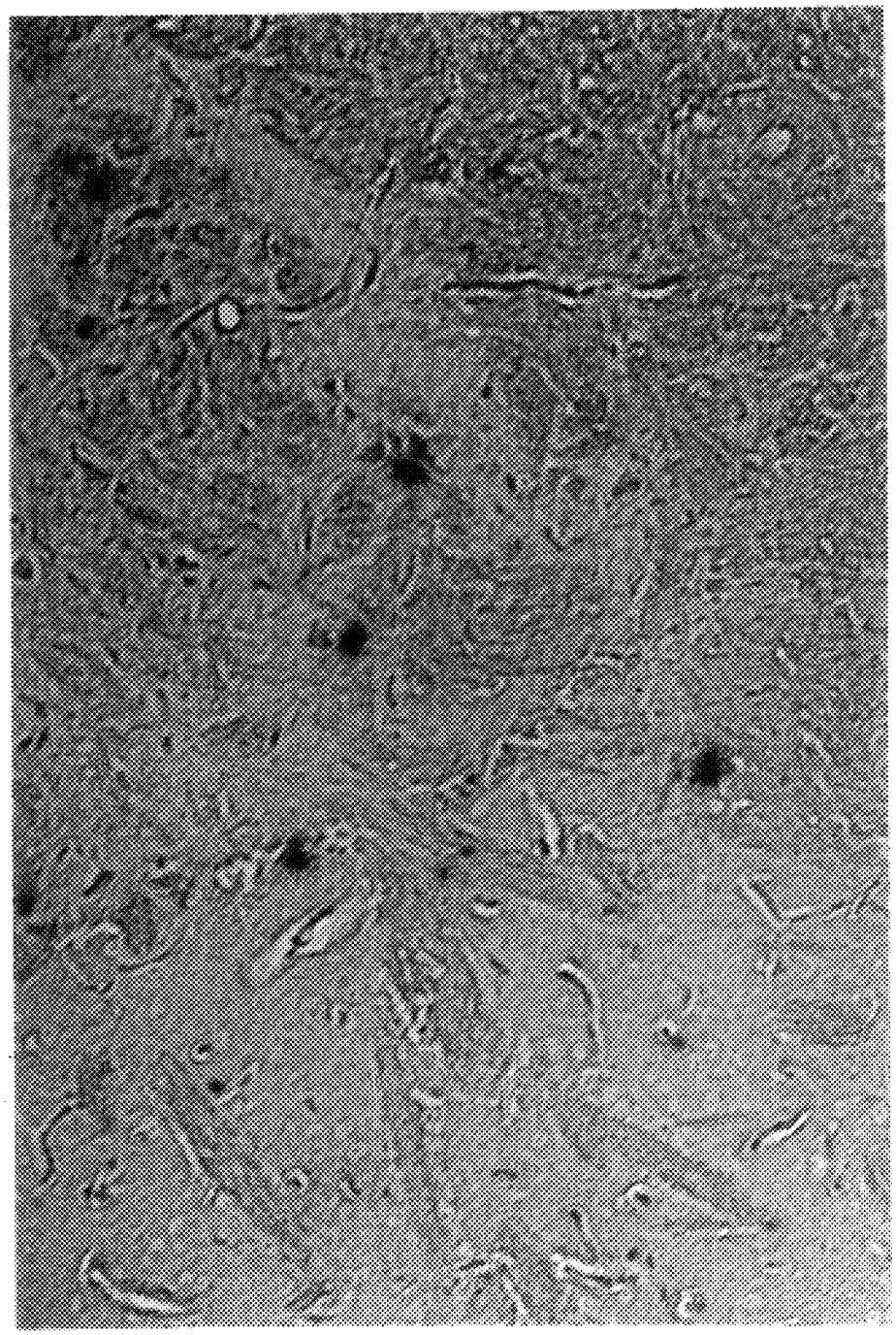

The results of this experiment are shown in FIG. 6. The histological slides show regions of PrP-associated plaques identified with the anti-PrP antiserum (FIG. 6B). PrP is the purified scrapie protein that acts as the infectious agent, and that is associated with amyloid deposition in affected subjects. The anti-AGE antiserum generated against AGE-RNase also decorated the amyloid plaques. A control antiserum (anti-RNase) did not react with the histological samples.

These results indicate that the AGEs are present in the amyloid plaques that are characteristic of spongiform encephalopathy. As the scrapie amyloid plaque forms, it acquires AGE modifications that are detectable by antibodies. AGE modification of the scrapie amyloid plaque can occur through AGE modification of soluble PrP or the amyloid plaque itself, or by both mechanisms.

EXAMPLE 3

Age-Modified Thioflavins

AGE-Thioflavin A, 3

2-(4-[([(6-aminohexyl)amino]carbonyl)amino]phenyl)-6-methylbenzothazole, 1, was prepared by combining 2-(4-amniophenyl)-6-methylbenzothiazole (0.48 g, Aldrich Chemical Company) with bis(trichloromethyl) carbonate (0.22 g) in xylene (10 ml), and heating the mixture at reflux for 3 hr. The not clear orange supernatant was decanted from some insoluble material and cooled, giving an orange suspension of 2-(4-isocyanatophenyl)-6-methylbenzothiazole. To this suspension was added 6-(t-butoxycarbonylamino)-1-hexylamine (0.40 g) in dichloromethane (10 ml). The mixture was stirred for 2 hr at room temperature (RT), forming a buff-colored suspension. The suspension was filtered and the solid washed with dichloromethane and t-butyl methyl ether to give 1 as an off-white powder, m.p. 164–165° C. This material (300 mg) was dissolved in 3 ml of 1:1 trifluoroacetic acid:dichloromethane and stirred for 4 hr at room temperature. The solvent was removed and the solid was partitioned between aqueous 0.1 N NaOH and dichloromethane. The organic layer was dried over sodium sulfate, filtered and concentrated. The residue was triturated with t-butyl methyl ether and filtered to yield 0.197 g of 1 as a white powder, m.p. 320° C.

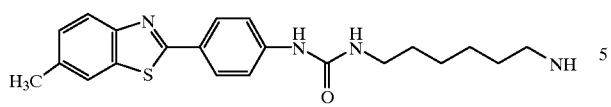

1

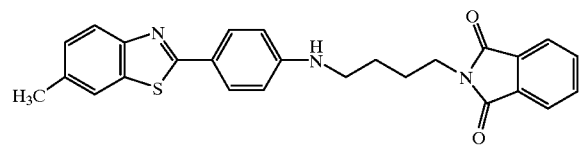

4

(4-[([(6-[(1-deoxy-2,3:4,5-di-O-isopropylidene-β-D-fructopyranos-1-yl)amino]hexyl)amino]carbonyl)amino]phenyl)-6-methylbenzothazole, 2, was prepared by dissolving 1 (0.196 g) and 2,3:4,5-bis-O-(1-methylethylidine)-aldehydo-β-D-arabino-hexos-2-ulo-2,6-pyranose (0.30 g, see 1987, Carbohydrate Research 167:123–130) in 8:1 methanol:water (4.5 ml) and treating the mixture with sodium cyanoborohydride (0.063 g) and acetic acid (0.040 ml). The resulting solution was stirred at 70° C. in an open flask for 6 hr. On cooling, a white solid separated. Filtration gave 0.276 g of 2 as a white solid, m.p. 144-146° C.

2-[4-(4-aminobutyl)aminophenyl]-6-methylbenzothiazole, 5, was prepared by heating 4 (0.20 g) with hydrazine hydrate (0.15 ml) in ethanol (20 ml) at 60° for 4 hr. Hydrochloric acid (1 ml) was added and the solution was heated at reflux for 1 hr. After cooling, phthalhydrazide was filtered out and the filtrate was concentrated, diluted with water, and neutralized with NaHCO₃. The precipitate was filtered and dried to give 5 in quantitative yield, m.p. 137–138° C.

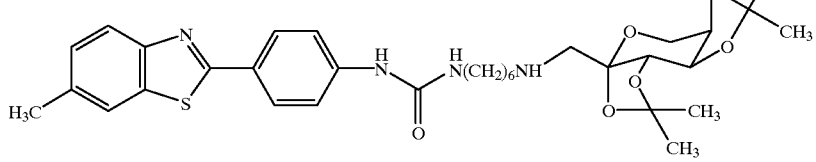

2

(4-[([(6-[(1-deoxy-β-D-fructopyranos-1-yl)amino]hexyl)amino]carbonyl)amino]-phenyl)-6-methylbenzothiazole, 3, was prepared by dissolving 2 (0.10 g) in 1,4-dioxane (4 ml), and treating the solution with water (4 ml) and conc. HCl (0.5 ml) with stirring at room temperature for 24 hr. Triethylamine (1 ml) was then added to the yellow solution, giving a turbid colorless mixture which was triturated and stored at 4° C. The resulting white powdery precipitate was filtered out and characterized as the 2,3-monoacetonide. The monoacetonide (0.025 g) was dissolved in 1.1 ml of 1.2 N HCl and stirred at 55° C. for 24 hr. Solid NaHCO₃ was added until the yellow color disappeared. Dichloromethane (1 ml) was added, and the mixture was stirred until a white powder separated. Filtration gave 15 mg of 3.

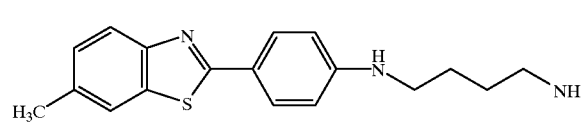

5

(4-[(4-[(1-deoxy-2,3:4,5-di-O-isopropylidene-β-D-fructopyranos-1-yl)amino]butyl)amino]phenyl)-6-methylbenzothiazole, 6, was prepared by refluxing 5 and 2,3:4,5-bis-O-(1-methylethylidine)-aldehydo-β-D-arabino-hexos-2-ulo-2,6-pyranose (1.0 g) in methanol for 3 hr. The solution was cooled and sodium cyanoborohydride (0.11 g)

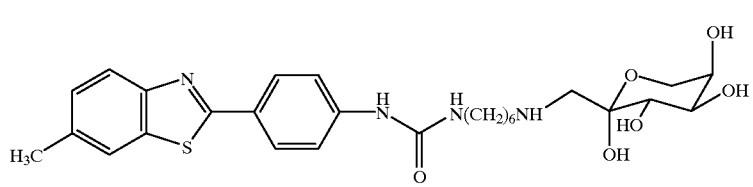

3

AGE-Thioflavin B. 8

2-[4-(4-phthalimidobutyl)aminophenyl]-6-methylbenzothiazole, 4, was prepared by dissolving 2-(4-aminophenyl)-6-methylbenzothiazole (0.139 g) and N-(4-bromobutyl)phthalimide (0.082 g) in dimethylforamide (DMF, 5 ml) and heating at reflux under nitrogen for 4 hr. The solution was cooled and treated with 5 ml of water. The yellow precipitate was filtered out and recrystallized from dichloromethane to give 0.090 g of 4, m.p. 169–170° C.

was added. The mixture was then refluxed for 2 hr. After cooling, the solvent was evaporated and the residue was partitioned between water and dichloromethane. The organic layer was washed with water, dried over sodium sulfate, and evaporated. The residue was chromatographed on silica gel using 20% ethyl acetate in dichloromethane. The product fractions were concentrated to a gum which crystallized on trituration with methanol. Filtration gave 0.445 g of 6 as a white solid, m.p. 129° C.

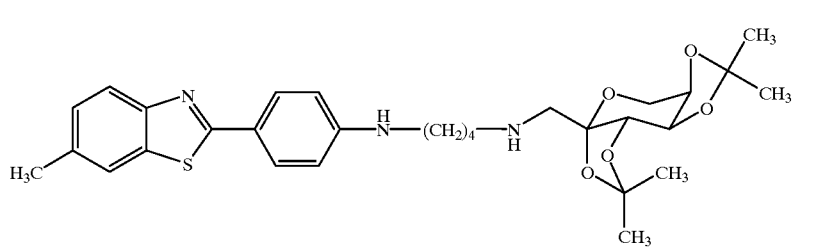

6

(4-[N-(4-[N-(1-deoxy-β-D-fructopyranos-1-yl)amino]butyl)-amino]phenyl)-6-methylbenzothiazole chloride, 6a, was prepared by dissolving 7 (0.025 g) in 8 ml 1:1 methanol/water containing 1.3 mL conc. HCl and stirring at RT under nitrogen for 24 hours. The solution was neutralized with aq. NaHCO$_3$, concentrated to 2 mL, filtered to remove precipitated salt, and purified by HPLC on a preparative C-18 reverse phase silica gel column using a gradient of 70–100% methanol in water. Compound 6a was collected in the peak of retention time of 23.1 minutes. Proton NMR (CD$_3$OD) δ 1.66 (br, CH$_2$CH$_2$CH$_2$NHCH$_2$), 2.46 (s, CH$_3$Ar), 2.68 (m, CH$_2$CH$_2$NHCHD, ca. 2.84 (2d, CH$_2$CH$_2$NHCH$_2$), 3.8 (t, ArNHCH$_2$), 3.55–4.05 (several m, 5H, carbohydrate C3–C6 protons), 6.70 (d, 2 aryl H ortho to NH), 7.28 (d, benzothiazole C5-H), 7.71 (s, benzothiazole C7—H), 7.76 (d, benzothiazole C4-H), 7.80 (d, 2 aryl H meta to NH).

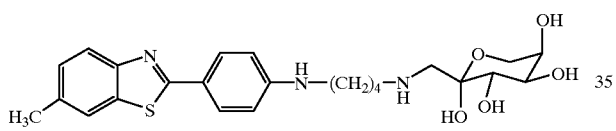

6a (4-[N-(4-[N-(1-deoxy-2,3:4,5-di-O-isopropylidene-β-D-fructopyranos-1 -yl)-N,N-dimethylammonio]butyl)-amino]phenyl)-6-methylbenzothiazole iodide, 7, was prepared by dissolving 6 (0.020 g) in acetone (2 ml), containing KHCO$_3$ (8 mg) and treating the solution with methyl iodide (0.200 ml) at RT overnight. The mixture was filtered and the filtrate was evaporated to give 7 as a yellow solid in quantitative yield. Recrystallization from dichloromethane/ether gave yellow crystals, m.p. 142° C.

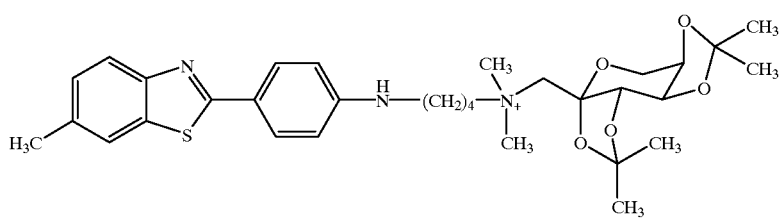

7

(4-[N-(4-[N-(1 -deoxy-β-D-fructopyranos-1-yl)-N,N-dimethylammonio]butyl)amino]phenyl)-6-methylbenzothiazole chloride, 8, was prepared by dissolving 7 (0.050 g) in 20 ml 1:1 methanol/water containing 3.5 ml conc. HCl and heating at 50° C. under nitrogen for 18 hr. The solution was neutralized with aq. NaHCO$_3$, concentrated to 5 ml, and filtered to remove precipitated salt. Of this 2 ml was purified by HPLC on a preparative C-18 reverse phase silica gel column using a gradient of 70–100% methanol in water. Compound 8 was collected in the peak of retention time of 13.5 minutes. Proton NMR δ 1.72 (m, CH$_2$C H$_2$CH$_2$NHCH$_2$), 1.95 (m, CH$_2$CH$_2$CH$_2$NHCH$_2$), 2.46 (s, C H$_3$Ar), ca. 3.34 (s, —N$^+$(CH$_3$)$_2$—), 3.4–4.1 (several m, 9H, carbohydrate C3–C6 protons and CH$_2$NCH$_2$), 6.70 (d, 2 aryl H ortho to NH), 7.28 (d, benzothiazole C5—H), 7.71 (s, benzothiazole C7—H), 7.76 (d, benzothiazole C4—H), 7.80 (d, 2 aryl H meta to NH).

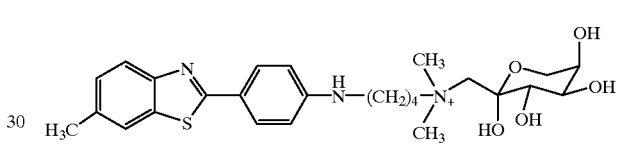

8

EXAMPLE 4

A Thioflavin-T Amadori Product Binds Amyloid

The present Example demonstrates that a modified Thioflavin-T, to which an Amadori product has been conjugated, co-precipitates with β-amyloid in vitro. This observation demonstrates the feasibility of linking an Amadori product or AGE to Thioflavin-T for targeting to amyloid deposits.

A preparation of Compound 8, supra, was employed in this assay. Soluble β-amyloid peptide was allowed to aggregate in the presence of phosphate buffer, Compound 8 or dithionitrobenzene and various compounds as described in Example 1, supra. The samples containing dithionitrobenzene are controls for non-specific association of a chromophoric small molecule with precipitated β-amyloid peptide. An additional control sample was prepared containing phosphate buffer and the various compounds, but lacking β-amyloid peptide. After overnight incubation, the tubes were centrifuged at 15,000×g for 30 minutes, half of the supernatant removed and added to a cuvette, and the absorbance spectrum of the supernatant from 200 to 600 nm obtained. In the absence of an association between compound 8 and aggregated sedimentable B-amyloid components of the aggregated assay incubation, compound 8, which has an absorbance maximum at about 350 nm, will remain in the supernatant and its presence and concentration can be readily determined. Alternatively, association of Compound 8 with the precipitated β-amyloid peptide would result in decreased absorbance at 350 nm. Thus, a decrease in the absorbance at 350 nm indicates that Compound 8 binds to fibrillar β-amyloid that sediments during centrifugation under these conditions, as shown in Example 1, supra. In the control tubes, no decrease in the absorbance is expected, since the compound should remain soluble.

Figure 7A:
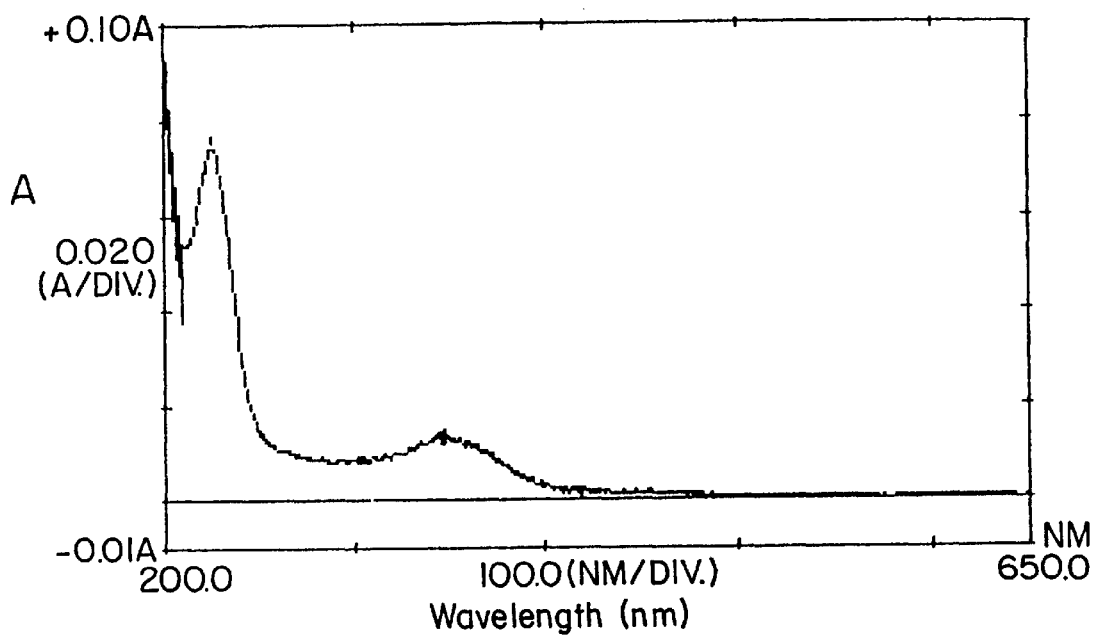
FIG. 7 presents absorption spectral data relating to association of a Thioflavin-T-Amadori product conjugate with fibrillar β-amyloid peptide in vitro. (A) Absorption spectrum of Thioflavin from 200 to 650 nm after pelleting of fibrillar β-amyloid peptide. (B) Absorption spectrum of Thioflavin-T before pelleting. (C) Absorption spectrum of dithionitrobenzene after pelleting. (D) Absorption spectrum of dithionitrobenzene before pelleting.
Figure 7B:
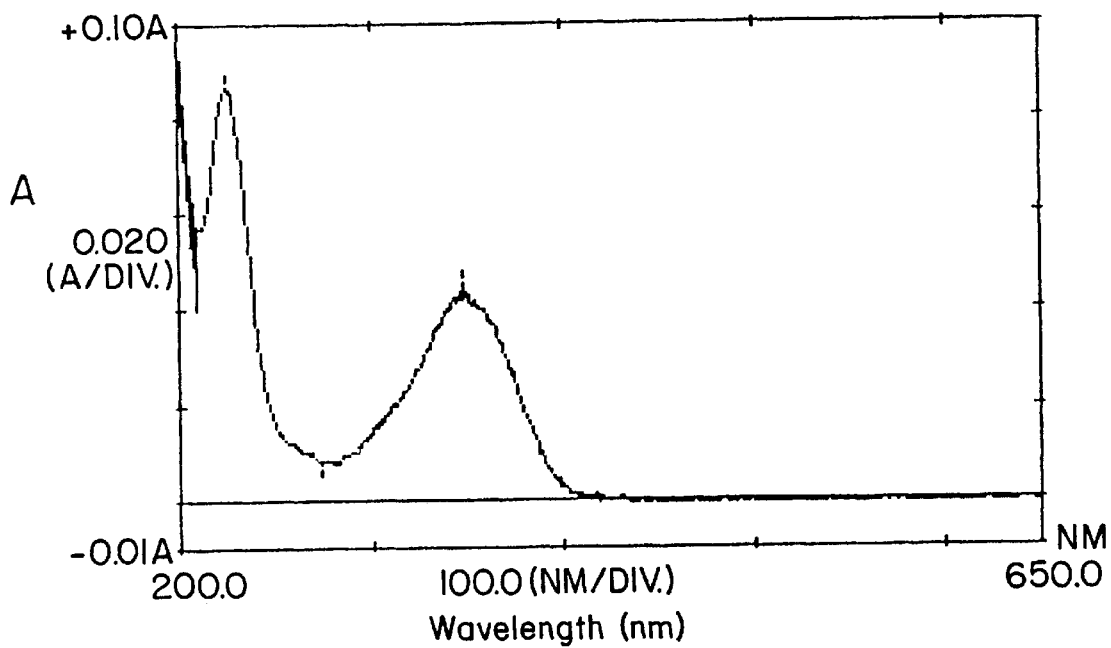
Figure 7C:
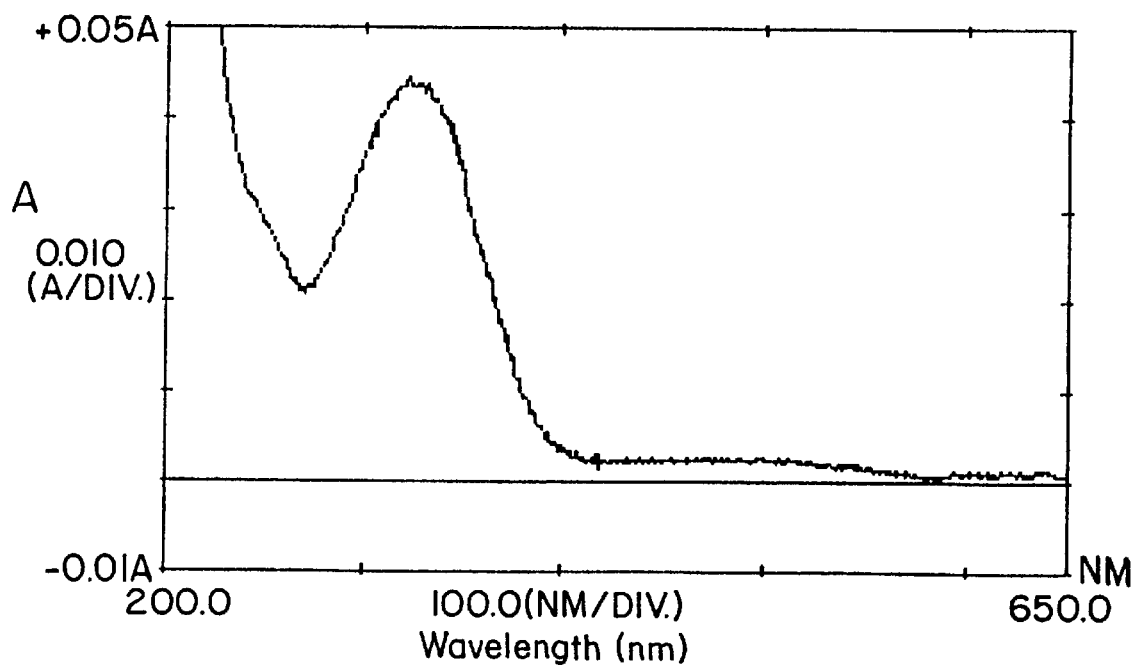
Figure 7D:
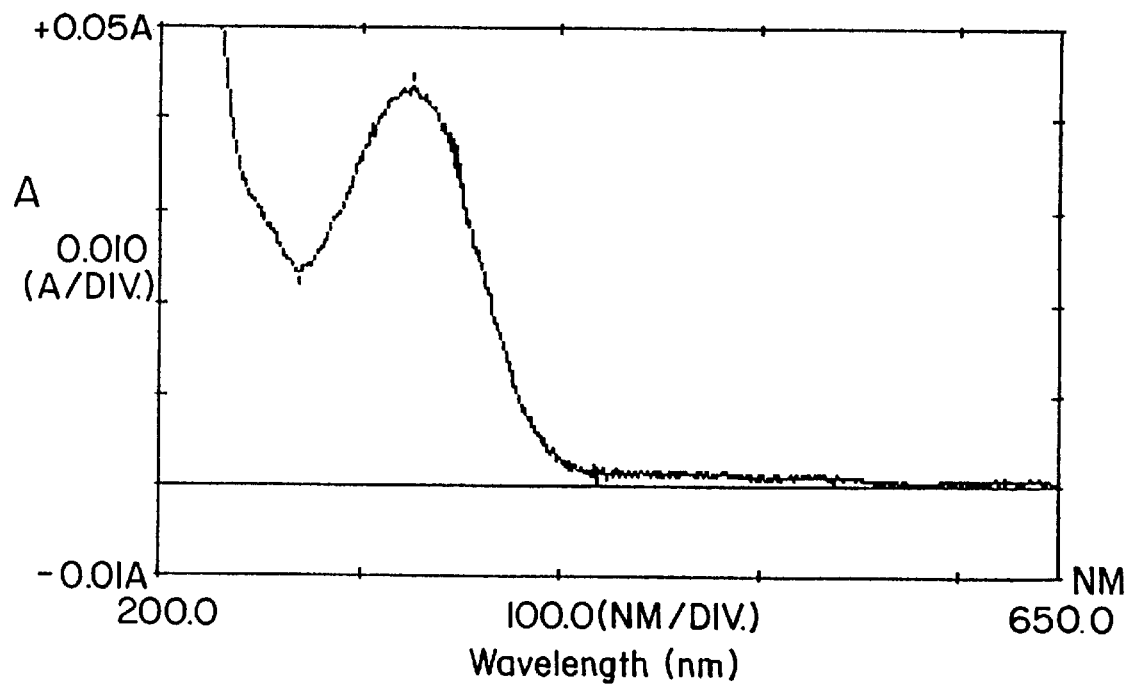

FIG. 7A shows that the absorbance at 350 nm of a supernatant solution containing Compound 8 is reduced when fibrillar β-amyloid peptide present in the solution was pelleted, compared to the absorbance prior to pelleting (FIG. 7B). In contrast, the absorbance of dithionitrobenzene, which has not been reported to bind to aggregated β-amyloid peptide deposits, does not decrease in the β-amyloid peptide sample supernatant compared to the control (compare FIG. 7C—pellet formation—with 7D—no pellet formation). These data indicate that compound 8 specifically associates with insoluble, aggregated β-amyloid peptide deposits.

EXAMPLE 5

Age-Amyloid in Type Ii Diabetes

Type II diabetes is characterized by deposits of aggregated amylin peptide in the pancreas. After a concentration-dependent lag period during in vitro incubations, soluble preparations of synthetic amylin slowly form fibrillar aggregates that resemble natural amyloid (Lorenzo et al., 1994, Nature 368:756–760) and are measurable by electron microscopy or by Congo Red birefringence under polarized light (Fraser et al., 1991, Biophys. J. 90:1194–1201). Aggregation of soluble amylin in these in vitro assays is expected to be enhanced by addition of small amounts of pre-aggregated amylin "seed" material. These seeds have also been prepared herein using a naturally occurring reaction between glucose and protein amino groups resulting in the formation of advanced glycosylation endproducts (AGEs) which chemically crosslink proteins. AGE-modified amylin-nucleation seeds are expected to further accelerate aggregation of soluble amylin compared to non-modified "seed" material. Over time, nonenzymatic advanced glycosylation, which is likely to occur at lysine-1 of amylin, and may occur at arginine-10, also results in the gradual accumulation of a set of post-translational covalent adducts on long-lived proteins in vivo. Using a standardized competitive ELISA assay, plaque fractions of Type II pancreatic islet cells are expected to be found to contain more AGE adducts per mg protein than found in like preparations from healthy, age-matched controls. These results indicate that the in vivo half-life of amylin is prolonged in Type II diabetes, resulting in greater accumulation of AGE modifications, which in turn can act to promote accumulation of additional amyloid.

Materials and Methods

Aggregation and Seeding Reactions.

Synthetic, HPLC-purified peptides representing the 37 amino acid human or cat islet amyloid polypeptide or amylin may be obtained by synthesis or from a commercial source, such as Bachem (Torrance, Calif.) or Peninsula Laboratories. Quantitative aggregate formation with sub-millimolar amylin concentrations may be detected using the procedure of LeVine (1992, Protein Science 2:404–410). Briefly, fluorescence of aggregates added to 10 μM Thioflavin-T (Aldrich)/50 mM potassium phosphate buffer, pH 6.0, can be measured upon excitation at 450±5 nm, and detection of emission at 482±10 nm on a Perkin Elmer LS-50B spectrofluorimeter. Alternatively, Congo red birefringence under polarized light can be used to detect aggregation (Fraser et al., supra). Small amounts of pre-formed aggregates or "nucleation seeds" are added to the soluble amylin and aggregation initiated, e.g., with 0.1 M sodium acetate.

Generations of "Seeds".

Soluble amylin (250 /AM) and 0.2 M sodium phosphate buffer, pH 7.5, are incubated with or without 1 M glucose at 37° C. to generate pre-formed aggregates of AGE-amylin referred to as "AGE-amylin seed" or "amylin seed," respectively. After incubation, protein concentrations of seed preparations are measured and adjusted with buffer to 150 /AM final concentration. Using competitive ELISA (Makita et al., supra), AGE content of an AGE-amylin seed and amylin-seed can be determined. Glucose and/or aminoguanidine, a potent inhibitor of advanced glycation and crosslink formation (Brownlee et al, 1986, Science 232:1629–1632), are also added to solutions of amylin before sodium acetate in some experiments to evaluate whether these AGE inhibitors inhibit seed formation.

Aggregation of amylin at lower (physiological) concentrations may be quantitated by the method of Burdick et al. (1992, J. Biol. Chem. 267:546–554). Synthetic preparations of amylin are labeled with $^{125}$I (NEN) and chloramine-T (Sigma) for 1 minute before the reaction was quenched with 10 mM tyrosine and sodium meta-bisulfite. Unincorporated label is removed by filtration through a SEPHADEX G-10 column equilibrated in 0.5×phosphate buffered saline (PBS), pH 7.4. The $^{125}$I-labeled amylin is immediately diluted to 5 nM final concentration in the presence of various "seeds," glucose and/or aminoguanidine at the indicated concentrations. After various incubation periods at 37° C., aggregation reactions are underlayed with 20% sucrose/0.1 M sodium acetate at the same pH as the incubation mixture, centrifuged for 30 minutes at 50,000×g, and frozen in liquid nitrogen. Each microfuge tube is cut and the bottom 5 mm representing the aggregated sedimentable fraction which have pelleted through the sucrose cushion, is counted in a gamma counter. The remainder of the tube and liquid are also counted. The amount of aggregate formed is calculated as a percentage equal to the number of counts in the pellet divided by the total number of counts per tube (pellet+ remainder) multiplied by 100.

Measurement of AGEs with Competitive ELISA.

Aliquots of pancreas containing amyloid fibrils from patients with and without Type II diabetes are resuspended in 2% sodium dodecylsulfate (SDS)/0.1 M β-mercaptoethanol (ME), and Dounce homogenized. The homogenate is boiled for 10 minutes and then centrifuged at 10,000×g for 10 minutes. Supernatants are aspirated and the resulting pellets washed three times with PBS at 10,000×g for 10 minutes. This crude plaque fraction may be further washed twice with 4 M urea and twice more with PBS before protease digestion. PBS-washed pellets are resuspended in PBS and 0.1% Proteinase-K (Boehringer Mannheim), digested overnight at 37° C. and heat inactivated at 75° C. for 3 hours. Quadruplicate aliquots of different amounts of plaque-containing pellet fractions are assayed for AGE content using a competitive ELISA (Makita et al., 1992, J. Biol. Chem. 267:5133–38), against standardized preparation of AGE-modified bovine serum albumin (AGE-BSA). Only values in the linear range of the standard curve should be included in the analyses.

Alternatively, tissue samples or amyloid fibril extracts can be prepared as described (Westermark et al., 1986, Biochem. Biophys. Res. Commun. 140:827–831; Westermark et al., 1987, Proc. Natl. Acad. Sci. USA 84:3881–85; Westermark et al., 1987, Am. J. Physiol. 127:414–417; Cooper et al., 1987, Proc. Natl. Acad. Sci. USA 84:8628–32).

Protein amounts may be quantitated with micro-BCA kit (Pierce) and with fluorescamine (Bohlen et al., 1973, Arch. Biochem. Biophys. 155:213–220). AGE Units are interpolated from a standard dilution curve of AGE-BSA and divided by the sample protein concentration to give AGE Units per mg protein. Statistical analysis using Student's test can be performed with the StatWorks program for Macintosh using a Macintosh personal computer (Apple Computer, Inc.).

Results

This experiment is expected to show that an AGE-amyloid seed comprising AGE-modified amylin will increase the rate of amylin aggregation. Similarly, soluble AGE-amylin is expected to aggregate more readily than soluble amylin. These results will indicate that, as discussed in Example 1, supra, with respect to βAP aggregation in Alzheimer's disease, AGE-modification of amylin plays a role in pathogenic amyloidosis associated with Type II diabetes.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

Various references are cited throughout this specification, each of which is incorporated herein by reference in its entirety.

What is claimed is:

1. A method for inhibiting AGE-amyloid-dependent aggregation of amyloid peptide and consequent amyloidogenesis in mammal comprising administering to sand mammal an effective amyloid aggregating inhibiting amount of an AGE-amyloid formation-inhibiting agent selected from the group consisting of aminoguanidine, α-hydrazinohistidine, lysine, an analog of aminoguanidine, a pharmaceutically acceptable acid addition salt of al analog of aminoguanidine, and mixtures thereof, said analog selected from hydrazine derivatives of the formula:

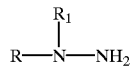

wherein R is a group of the formula

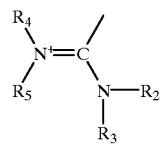

and $R_1$ is hydrogen or a lower alkyl group of 1–6 carbon atoms, a hydroxyethyl group, or together with $R_2$ may be a lower alkylene bridge of 24 carbon atoms; $R_2$ is hydrogen or a lower group alkyl of 1–6 carbon atoms or together with $R_1$ or $R_3$ is a lower alkylene bridge of 2–4 carbon atoms, amino, hydroxy, or an aminoalkylene group of the formula

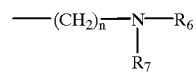

wherein n is an integer of 2–7 and $R_6$ and $R_7$ are independently a lower alkyl group of 1–6 carbon atoms or together form a part of a cycloalkyl or heterocyclic ring containing from 1 to 2 heteroatoms, of which at least one is nitrogen; and the second of said heteroatoms is selected from the group consisting of nitrogen, oxygen, and sulfur, with the proviso that when the second of said heteroatoms of the heterocyclic ring is nitrogen and forms a piperazine ring; said second heteroatom may be optionally substituted by a substituent that is identical to the portion of the compound on the first nitrogen of the piperazine ring; $R_3$ is hydrogen, a lower alkyl group of 1–6 carbon atoms, or together with $R_2$ or $R_4$ is a lower alkylene bridge of 2–4 carbon atoms; $R_4$ is hydrogen, a lower alkyl group of 1–6 carbon atoms or together with $R_3$ is a lower alkylene bridge of 2–4 carbon atoms; or an amino group; $R_5$ is hydrogen, or a lower alkyl group of 1–6 carbon atoms; with the proviso that at least one of $R_1$, $R_2$, $R_3$, $R_4$ or $R_5$ is other than hydrogen; or R is an acyl or a lower alkylsulfonyl group of up to 10 carbon atoms and $R_1$ is hydrogen.

2. The method of claim 1, wherein said compound is administered intraventricularly, intracranially, intraperitoneally, intravenously, intra-arterially, nasally, or orally.

3. The method of claim 1 wherein said amyloid peptide is selected from the group consisting of amylin, β-amyloid peptide, and prion protein.

4. A method for inhibiting AGE-amyloid-dependent aggregation of amyloid peptide and consequent amyloidogenesis in a mammal comprising administering to said mammal an effective amyloid aggregating inhibiting amount of an AGE-amyloid formation-inhibiting agent selected from the group consisting of aminoguanidine, α-hydrazinohistidine, lysine, an analog of aminoguanidine, a pharmaceutically acceptable acid addition salt of an analog of aminoguanidine, and mixtures thereof.

5. The method of claim 4 wherein said analog of aminoguanidine is a hydrazine derivative of the formula:

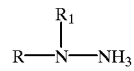

wherein R is a group of the formula

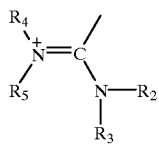

and $R_1$ is hydrogen or a lower alkyl group of 1–6 carbon atoms, a hydroxyethyl group, or together with $R_2$ may be a lower alkylene bridge of 2–4 carbon atoms; $R_2$ is hydrogen or a lower group alkyl of 1–6 carbon atoms or together with $R_1$ or $R_3$ is a lower alkylene bridge of 2–4 carbon atoms, amino, hydroxy, or an aminoalkylene group of the formula

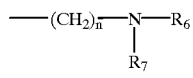

wherein n is an integer of 2–7 and $R_6$ and $R_7$ are independently a lower alkyl group of 1–6 carbon atoms or together form a part of a cycloalkyl or heterocyclic ring containing from 1 to 2 heteroatoms, of which at least one is nitrogen; and the second of said heteroatoms is selected from the group consisting of nitrogen, oxygen, and sulfur; with the proviso that when the second of said heteroatoms of the heterocyclic ring is nitrogen and forms a piperazine ring; said second heteroatom may be optionally substituted by a substituent that is identical to the portion of the compound on the first nitrogen of the piperazine ring; $R_3$ is hydrogen, a lower alkyl group of 1–6 carbon atoms, or together with $R_2$ or $R_4$ is a lower alkylene bridge of 2–4 carbon atoms; $R_4$ is hydrogen, a lower alkyl group of 1–6 carbon atoms or together with $R_3$ is a lower alkylene bridge of 2–4 carbon atoms; or an amino group; $R_5$ is hydrogen, or a lower alkyl group of 1–6 carbon atoms; with the proviso that at least one of $R_1, R_2, R_3, R_4$ or $R_5$ is other than hydrogen; or R is an acyl or a lower alkylsulfonyl group of up to 10 carbon atoms and $R_1$ is hydrogen.

* * * * *